US009901621B2

(12) United States Patent
Jung et al.

(10) Patent No.: US 9,901,621 B2
(45) Date of Patent: *Feb. 27, 2018

(54) COMPOSITION FOR TREATING HYPERLIPIDEMIA COMPRISING OXYNTOMODULIN DERIVATIVE

(71) Applicant: HANMI PHARM. CO., LTD., Hwaseong-si, Gyeonggi-do (KR)

(72) Inventors: Sung Youb Jung, Suwon-si (KR); Jin-Sun Kim, Yongin-si (KR); Myung Hyun Jang, Seoul (KR); Sang Hyun Lee, Seoul (KR); In Young Choi, Yongin-si (KR); Se Chang Kwon, Seoul (KR)

(73) Assignee: Hanmi Pharm. Co., Ltd., Hwaseong-Si, Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/086,499

(22) Filed: Mar. 31, 2016

(65) Prior Publication Data

US 2016/0199451 A1 Jul. 14, 2016

Related U.S. Application Data

(62) Division of application No. 14/415,200, filed as application No. PCT/KR2013/006668 on Jul. 25, 2013, now abandoned.

(30) Foreign Application Priority Data

Jul. 25, 2012 (KR) .................. 10-2012-0081475

(51) Int. Cl.
| | |
|---|---|
| *A61K 38/22* | (2006.01) |
| *A61K 47/48* | (2006.01) |
| *A61K 38/26* | (2006.01) |
| *C07K 14/605* | (2006.01) |
| *A61P 3/06* | (2006.01) |
| *A61K 45/06* | (2006.01) |
| *C07K 14/76* | (2006.01) |
| *C07K 14/78* | (2006.01) |
| *A61K 47/60* | (2017.01) |
| *A61K 47/59* | (2017.01) |
| *A61K 47/64* | (2017.01) |
| *A61K 47/68* | (2017.01) |

(52) U.S. Cl.
CPC .............. *A61K 38/26* (2013.01); *A61K 38/22* (2013.01); *A61K 45/06* (2013.01); *A61K 47/59* (2017.08); *A61K 47/593* (2017.08); *A61K 47/60* (2017.08); *A61K 47/643* (2017.08); *A61K 47/6435* (2017.08); *A61K 47/68* (2017.08); *A61K 47/6811* (2017.08); *C07K 14/605* (2013.01); *C07K 14/76* (2013.01); *C07K 14/78* (2013.01)

(58) Field of Classification Search
CPC .. A61K 38/26; A61K 47/48415; A61K 38/22; A61K 47/48369; A61K 47/48192; A61K 47/482; A61K 47/48215; A61K 47/48292; A61K 45/06; A61K 47/48284; A61K 47/60; A61K 47/59; A61K 47/593; A61K 47/643; A61K 47/6435; A61K 47/68; A61K 47/6811; C07K 14/605; C07K 14/76; C07K 14/78

See application file for complete search history.

(56) References Cited

U.S. PATENT DOCUMENTS

| | | | |
|---|---|---|---|
| 7,217,845 | B2 | 5/2007 | Rosen et al. |
| 7,521,424 | B2 | 4/2009 | Rosen et al. |
| 7,737,260 | B2 | 6/2010 | Kim et al. |
| 7,928,058 | B2 | 4/2011 | Sinha Roy et al. |
| 8,729,017 | B2 | 5/2014 | DiMarchi |
| 8,778,872 | B2 | 7/2014 | DiMarchi et al. |
| 2004/0087778 | A1 | 5/2004 | Feige et al. |
| 2009/0238838 | A1 | 9/2009 | Kim et al. |
| 2009/0298757 | A1 | 12/2009 | Bloom et al. |
| 2010/0190701 | A1 | 7/2010 | Day et al. |
| 2010/0196405 | A1 | 8/2010 | Ng |
| 2010/0330108 | A1 | 12/2010 | Song et al. |
| 2011/0034374 | A1 | 2/2011 | Bloom et al. |
| 2011/0065633 | A1 | 3/2011 | DiMarchi et al. |
| 2011/0152182 | A1 | 6/2011 | Alsina-Fernandez et al. |
| 2012/0003712 | A1 | 1/2012 | Song et al. |
| 2012/0165503 | A1 | 6/2012 | Carrington et al. |
| 2012/0329707 | A1 | 12/2012 | DiMarchi et al. |
| 2013/0035285 | A1 | 2/2013 | Lau et al. |

FOREIGN PATENT DOCUMENTS

| | | |
|---|---|---|
| CN | 101213209 A | 7/2008 |
| CN | 101389648 A | 3/2009 |
| CN | 101578107 A | 11/2009 |
| CN | 101974077 A | 2/2011 |
| CN | 102010473 A | 4/2011 |

(Continued)

OTHER PUBLICATIONS

US 8,729,011, 05/2014, DiMarchi et al. (withdrawn)

(Continued)

*Primary Examiner* — Julie Ha
*Assistant Examiner* — Li Ni Komatsu
(74) *Attorney, Agent, or Firm* — Baker & Hostetler LLP

(57) ABSTRACT

The present invention relates to a composition for preventing or treating hyperlipidemia, fatty liver disease or arteriosclerosis, comprising an oxyntomodulin derivative as an active ingredient. The oxyntomodulin derivative has a high ability to activate GLP-1 receptor and glucagon receptor compared to native oxyntomodulin and has the effects of reducing the blood total cholesterol, low-density cholesterol and triglyceride levels that were increased by high-fat diet, and increasing high-density cholesterol levels and the high-density cholesterol/low-density cholesterol ratio. Thus, the oxyntomodulin derivative can be effectively used for the treatment of hyperlipidemia and related diseases.

15 Claims, 4 Drawing Sheets

(56) References Cited

FOREIGN PATENT DOCUMENTS

| | | |
|---|---|---|
| CN | 102369209 A | 3/2012 |
| CN | 103732616 A | 4/2014 |
| CN | 103732618 A | 4/2014 |
| EP | 2300037 | 3/2011 |
| EP | 2330124 | 6/2011 |
| EP | 1 891 105 B1 | 4/2012 |
| JP | 2003-531632 A | 10/2003 |
| JP | 2008-543816 A | 12/2008 |
| JP | 2009-527558 A | 9/2009 |
| JP | 2009-203235 A | 12/2009 |
| JP | 2011-511753 A | 8/2010 |
| JP | 2013-537525 A | 2/2011 |
| KR | 10-2005-0026685 A | 3/2005 |
| KR | 10-2006-0106486 A | 10/2006 |
| KR | 10-2008-0039375 A | 5/2008 |
| KR | 10-2009-0098843 A | 9/2009 |
| KR | 10-2011-0039230 A | 4/2011 |
| KR | 10-2009-0096498 A | 5/2012 |
| KR | 10-2012-0043208 A | 5/2012 |
| KR | 10-2012-0052973 A | 5/2012 |
| KR | 10-2014-0018462 A | 2/2014 |
| WO | WO 03/022304 A | 3/2003 |
| WO | WO 03/022304 A1 | 3/2003 |
| WO | WO 2005/035761 A1 | 10/2003 |
| WO | WO 2004/062685 A2 | 7/2004 |
| WO | WO 2005/087797 A1 | 9/2005 |
| WO | WO 2006/059106 A2 | 6/2006 |
| WO | WO 2006/134340 A2 | 12/2006 |
| WO | WO 2007/022123 A2 | 2/2007 |
| WO | 2007/100535 A2 | 9/2007 |
| WO | WO 2007/146038 A2 | 12/2007 |
| WO | WO 2008/071972 A1 | 6/2008 |
| WO | WO 2008/082274 A1 | 7/2008 |
| WO | WO 2008/101017 A2 | 8/2008 |
| WO | 2009/033756 A2 | 3/2009 |
| WO | WO 2009/058734 A1 | 5/2009 |
| WO | WO 2009/069983 A2 | 6/2009 |
| WO | WO 2009/099763 A1 | 8/2009 |
| WO | WO 2009/155257 A1 | 12/2009 |
| WO | WO 2009/155258 A1 | 12/2009 |
| WO | WO 2010/013012 A2 | 2/2010 |
| WO | WO 2010/033207 A1 | 3/2010 |
| WO | WO 2010/033220 A1 | 3/2010 |
| WO | WO 2010/070253 A1 | 6/2010 |
| WO | WO 2010/071807 A1 | 6/2010 |
| WO | WO 2010/096052 A1 | 8/2010 |
| WO | WO 2010/096142 A1 | 8/2010 |
| WO | 2010/107256 A2 | 9/2010 |
| WO | WO 2010/108153 A2 | 9/2010 |
| WO | WO 2010/148089 A1 | 12/2010 |
| WO | WO 2011/006497 A1 | 1/2011 |
| WO | WO 2011/056713 | 5/2011 |
| WO | 2011/071957 A1 | 6/2011 |
| WO | 2011/075393 A1 | 6/2011 |
| WO | WO 2011/087671 | 7/2011 |
| WO | WO 2011/087672 | 7/2011 |
| WO | 2011/143208 A1 | 11/2011 |
| WO | WO 2012/057525 A2 | 5/2012 |
| WO | WO 2012/088379 A2 | 6/2012 |
| WO | 2012/173422 A1 | 12/2012 |
| WO | WO 2012/169798 A2 | 12/2012 |
| WO | WO 2013/157002 A1 | 10/2013 |
| WO | WO 2014/017843 | 1/2014 |
| WO | WO 2014/073842 | 5/2014 |

OTHER PUBLICATIONS

Eaton, Hypolipemic action of glucagon in experimental endogenous lipemia in the rat, Journal of Lipid Research, 1973, 14, pp. 312-318.*

Habegger et al, The metabolic actions of glucagon revisited, Nat. Rev. Endocrinol., 2010, 6, pp. 689-697.*

European Patent Office, Communication dated Feb. 25, 2016 in counterpart application No. 13823727.6.

International Searching Authority International Search Report for PCT/KR2013/006668 dated Oct. 21, 2013.

State Intellectual Property Office of the P.R.C., Communication dated Dec. 30, 2015 in counterpart application No. 201380039596. X.

Atherosclerosis, from http://www.merckmanuals.com/professional/cardiovascular-disorders/arteriosclerosis/atherosclerosis, pp. 1-14, accessed Dec. 29, 2015.

USPTO, Communication dated Jan. 20, 2016 in U.S. Appl. No. 14/415,200.

Day et al, Optimization of Co-Agonism at GLP-1 and Glucagon Receptors to Safely Maximize Weight Reduction in DIORodents, Peptide Science, 2012, 98, pp. 443-450, published online Apr. 14, 2012.

Definition of Arteriosclerosis, from http://www.merckmanuals.com/professional/cardiovascular-disorders/arteriosclerosis/defi . . . ,page 1, accessed Dec. 29, 2015.

Ding et al, Exendin-4, a Glucagon-Like Protein-1 (GLP-1) Receptor Agonist, Reverses Hepatic Steatosis in ob/ob Mice, Hepatology, 2006, 43, pp. 173-181.

Dyslipidemia, from http://www.merckmanuals.com/professional/endocrine-and-metabolic-disorders/lipid-dis . . . , pp. 1-11, accessed Dec. 29, 2015.

Exendin-4 sequence, from http://www.sigmaaldrich.com/catalog/product/sigma/e7144lang=en®ion=US, p. 1, accessed Dec. 28, 2015.

Fatty Liver Disease, from http://www.webmd.com/hepatitis/fatty-liver-diseasepage=2&print=true, pp. 1-4, accessed Dec. 29, 2015.

Nonatheromatous Arteriosclerosis, from http://www.merckmanuals.com/professional/cardiovasculardisorders/ arteriosclerosis/non . . . , pp. 1-2, accessed Dec. 29, 2015.

Vitamins & Supplements Search, from http://www.webmd.com/vitamins-supplements/condition-1275-Hyperlipidemia.aspx, pp. 1-3, accessed Dec. 29, 2015.

"Obesity Causes,", Obesity Prevention Source, http://www.hsph.harvard.edu/obesity-prevention-source/obesity-causes/, accessed Oct. 6, 2014, 1-3.

"Obesity", Merck Manual, http://://www.merckmanuals.com/professoinal/nutritional_disorders/obesity_and_the_metab., accessed Oct. 6, 2014, 1-9.

"Prescription Medications for the Treatment of Obesity", U.S. Department of Health and Human Services, Apr. 2013, 1-8.

"Water", http/://222.biology-online.org/dictionary/Water, accessed Apr. 24, 2014, 1-3.

"What Causes Overweight and Obesity?", National Heart, Lung, and Blood Institute, http://www.nhibi.nih.gov/health/health-topics/topics/obe/causes.html, accessed Oct. 6, 2014, 1-5.

"Definition of Prophylactic", Merriam Webster Dictionary, accessed Feb. 8, 2015, http://www.merriam-webster.com/dictionary/prophylactic, 1 page.

Berendsen, "A Glimpse of the Holy Grail?", Science, 1998, 282, 642-643.

Bradley et al., Limits of Cooperativity in a Structurally Modular Protein: Response of the Notch Ankyrin Domain to Analogous Alanine Substitutions in Each Repeat, 2002, 373-386.

Collie et al., "Purification and sequence of rat oxyntomodulin", Proc. Natl. Acad. Sci., Sep. 1994, vol. 91, 9362-9366.

Day et al., "A new glucagon and GLP-1 co-agonist eliminates obesity in rodents", Nature Chemical Biology, 2009, 6, 749-757.

Drucker, "Glucagon-Like Peptides", Diabetes, Feb. 1998, vol. 47, 159-169.

European Patent Office, "Supplementary European Search Report", dated Dec. 3, 2014, issued in counterpart Application No. 12797363.4, 5 pages.

European Patent Office, "Supplementary European Search Report", dated Oct. 13, 2014, issued in counterpart Application No. 12801247.3, 7 pages.

Federal Institute of Industrial Property, "Office Action", dated Dec. 4, 2015, issued in corresponding Russian Application No. 2013153198/10, 15 pages.

(56) References Cited

OTHER PUBLICATIONS

Federal Institute of Industrial Property, "Office Action", dated Dec. 4, 2015, issued in corresponding Russian Application No. 2013154066/10, 14 pages.
Frankel et al., "Characterization of diphtheria fusion proteins targeted to the human interleukin-3 receptor," Protein Engineering, 2000, vol. 13, No. 8, 575-581.
Goldberg, "Dyslipidemia", http://www.merckmanuals.com/professional/endocrine-and-metabolic-diorders/lipid-dis . . . , accessed Dec. 29, 2015, 1-11.
International Patent Application No. PCT/KR2012/004722: International Search Report and Written Opinion dated Nov. 14, 2012, 6 pages.
International Patent Application No. PCT/KR2013/009986: International Search Report dated Jan. 29, 2014, 11 pages.
International Patent Application No. PCT/KR2013/009990: International Search Report and Written Opinion dated Jan. 20, 2014, 12 pages.
Japan Patent Office, "Grounds for Rejection", dated Dec. 15, 2015, issued in corresponding Japanese Application 2014/515759, 12 pages.
Japan Patent Office, "Grounds for Rejection", dated Nov. 24, 2015, issued in corresponding Japanese Application No. 2014-514799, 9 pages.
Korean Intellectual Property Office, "Decision to Grant a Patent", dated Feb. 26, 2015, issued in corresponding Korean Application No. 10-2012-0061166, 5 pages.
Korean Intellectual Property Office, "Notice of Final Rejection", dated Aug. 28, 2014, issued in corresponding Korean Application No. 10-2012-0061166, 6 pages.
Korean Intellectual Property Office, "Notice of Preliminary Rejection", dated Sep. 30, 2013, issued in corresponding Korean Application No. 10-2012-0061166, 9 pages.
Korean Intellectual Property Office, "Notice of Preliminary Rejection", dated Nov. 20, 2014, issued in corresponding Korean Application No. 10-2012-0061166, 7 pages.
Machine Translation of Korean Publication: 1020100105494 A, dated Sep. 29, 2010, Hanmi Holdings Co. Ltd., 48 pages.
New Zealand Intellectual Property Office, "First Examination Report", dated Oct. 7, 2014, issued in corresponding application No. 618810, 3 pages.
New Zealand Intellectual Property Office, "Further Examination Report", dated Oct. 30, 2015, issued in corresponding application No. 618810, 4 pages.
Ngo et al., "Computational Complexity, Protein Structure Protection, and the Levinthal Paradox", The Protein Folding Problem and Tertiary Structure Prediction, 1994, 491-494.
Pocai et al., "Glucagon-like peptide 1/glucagon receptor dual agonism reverses obesity in mice", Diabetes, 2009, vol. 58, No. 10, 2253-2266.
Rudinger, "Characteristics of the amino acids as components of a peptide hormone sequence", Peptide Hormones, JA Parsons Ed., 1976, pp. 1-7.
Santoprete et al., "DPP-IV-resistant, long acting oxyntomodulin derivatives," Journal of Peptide Science, 2011, vol. 17, No. 4, 270-280.
Skosyrev et al., "The Dependence of Stability of the Green Fluorescent-Protein-Obelin Hybrids on the Nature of Their Constituent Modules and the Structure of the Amino Acid Linker," Russian Journal of Bioorganic Chemistry, 2001, vol. 27, No. 5, 323-329.
State Intellectual Property Office of PRC, "English translation of Notification of First Office Action", dated Mar. 6, 2015, issued in corresponding Chinese Application No. 201280038851.4, 7 pages.
State Intellectual Property Office of PRC, "Notification of First Office Action", dated Jan. 7, 2015 issued in corresponding Chinese Application No. 201280039781.4, 21 pages.
State Intellectual Property Office of PRC, "Notification of Second Office Action", dated Sep. 24, 2015, issued in corresponding Chinese Application No. 201280039781.4, 11 pages.
State Intellectual Property Office of PRC, "Notification of Second Office Action", dated Sep. 15, 2015, issued in corresponding Chinese Application No. 201280038851.4, 15 pages.
Taiwanese Intellectual Property Office, "Examination Report", dated Dec. 23, 2013 issued in corresponding application No. 101121483, 15 pages.
Treetharnmathurot et al., "Effect of PEG molecular weight and linking chemistry on the biological activity and thermal stability of PEGylated trypsin," International Journal of Pharmaceutics, 2008, vol. 357, 252-259.
U.S. Appl. No. 14/124,969: Communication dated Jun. 25, 2014, 12 pages.
U.S. Appl. No. 14/124,969: Final Rejection, dated Apr. 14, 2015, 17 pages.
U.S. Appl. No. 14/124,969: Non-Final Rejection, dated Dec. 10, 2014, 40 pages.
U.S. Appl. No. 14/126,914: Communication, dated Sep. 18, 2014, 14 pages.
U.S. Appl. No. 14/126,914: Examiner Initialed Interview, dated Feb. 29, 2016, 29 pages.
U.S. Appl. No. 14/126,914: Non-Final Rejection, dated Mar. 5, 2015, 35 pages.
U.S. Appl. No. 14/748,389: Non-Final Rejection, dated Jan. 13, 2016, 18 pages.
Voet et al., "Abnormal Hemoglobins", Biochemistry, John Wiley & Sons Inc., 1995, 235-241.
Vorobiev et al., "Chemical polysialylation: Design of conjugated human oxyntomodulin with a prolonged anorexic effect in vivo", Biochimie, 2013, vol. 95, 264-270.
Wynne et al., "Oxyntomodulin increases energy expediture in addition to decreasing energy intake in overweight and obese humans: a randomised controlled trial," International Journal of Obesity, 2006, 30, 1729-1736.
Wynne et al., "Subcutaneous Oxyntomodulin Reduces Body Weight in Overweight and Obese Subjects a Doube-Blind, Randomized, Controlled Trial," Diabetes, Aug. 2005, vol. 54, 2390-2395.
New Zealand Patent Application No. 718999: Further Examination Report dated Oct. 26, 2016, 3 pages.
Clark et al., "Identifying and Managing Patients with Hyperlipidemia", The American Journal of Managed Care, Aug. 1997, vol. 3, No. 8, 1211-1219.
Kerr et al., "(D-Ser$^2$)Oxm[mPEG-PAL]: A novel chemically modified analogue of oxyntomodulin with antihyperglycaemic, insulinotropic and anorexigenic actions", Biochemical Pharmacology, Dec. 2010, vol. 80, Issue 11, 1727-1735.
Shigeru, "Obesity and Metabolic Syndrome", Tokyo Internal Medical Association Seminar 2008 Special Lecture, Dec. 2008, vol. 24, No. 2, 8 pages.

\* cited by examiner

*: significant increase compared to high-fat diet group ($p<0.01$)

*: significant increase compared to high-fat diet group ($p<0.05$)

*$P<0.05$, $P<0.01$, *$P<0.001$ vs.HFD hamsters ed hyperlipidemia is caused by various disease conditions, drugs and dietary habits. In addition, hyperlipidemia is also caused by a combination of the primary and secondary causes of hyperlipidemia. As criteria for the diagnosis of hyperlipidemia, a total cholesterol level of 220 mg/dl or higher and a triglyceride level of 150 mg/dl or higher are generally used. -->

COMPOSITION FOR TREATING HYPERLIPIDEMIA COMPRISING OXYNTOMODULIN DERIVATIVE

CROSS REFERENCE TO RELATED APPLICATIONS

This application is a Divisional of U.S. application Ser. No. 14/415,200 filed Jan. 16, 2015, now abandoned, which is a National Stage of International Application No. PCT/KR2013/006668 filed Jul. 25, 2013, claiming priority based on Korean Patent Application No. 10-2012-0081475 filed Jul. 25, 2012, the contents of all of which are incorporated herein by reference in their entirety.

SEQUENCE LISTING

The instant application contains a Sequence Listing which has been submitted electronically in ASCII format and is hereby incorporated by reference in its entirety. The ASCII copy, created on Jun. 10, 2016, is named 106132.000154_SL.txt and is 39,938 bytes in size.

TECHNICAL FIELD

The present invention relates to a composition for preventing or treating hyperlipidemia, fatty liver disease or arteriosclerosis, which comprises an oxyntomodulin derivative as an active ingredient, and to a method for treating hyperlipidemia, fatty liver disease or arteriosclerosis using the composition.

BACKGROUND ART

In recent years, in Korea, the intake of fats from foods has increased due to economic growth and the westernization of eating habits, and metabolic diseases such as hyperlipidemia, diabetes, hypertension, arteriosclerosis and fatty liver disease, which are caused by a lack of exercise, have increased.

Hyperlipidemia refers to a condition associated with elevated levels of lipids, such as free cholesterol, cholesterol esters, phospholipids and triglycerides, in blood. Hyperlipidemia can appear in three forms: (1) hypercholesterolemia, (2) hypertriglyceridemia, and (3) combined hyperlipidemia (hypercholesterolemia and hypertriglyceridemia). Hyperlipidemia is generally classified into primary hyperlipidemia and secondary hyperlipidemia. Primary hyperlipidemia is generally caused by genetic defects, whereas secondary hyperlipidemia is caused by various disease conditions, drugs and dietary habits. In addition, hyperlipidemia is also caused by a combination of the primary and secondary causes of hyperlipidemia. As criteria for the diagnosis of hyperlipidemia, a total cholesterol level of 220 mg/dl or higher and a triglyceride level of 150 mg/dl or higher are generally used.

There are various forms of cholesterol that naturally occur in mammals. Low-density (LDL) cholesterol is known to be harmful to health, and it is known that an increase in LDL cholesterol increases the risk of heart disease (Assman et al., Am. J. Card, 1996). In addition, high-density (HDL) cholesterol is regarded as good cholesterol and is essential for health, because it prevents atherosclerosis or the like.

Although hyperlipidemia does not show specific symptoms by itself, excessive lipids in blood adhere to the blood vessel walls to reduce the blood vessel size and cause atherosclerosis by inflammatory reactions. For this reason, coronary heart disease, cerebrovascular disease, obstruction of peripheral blood vessels, etc., can occur (E. Falk et al., Circulation, 1995). In addition, excessive blood lipids are accumulated in liver tissue, and thus can cause fatty liver disease. The fatty liver refers to a condition in which the ratio of fats in the weight of the liver is more than 5%. The fatty liver can be caused not only by excessive intake of fats, but also by intake of alcohol.

Current methods that are used to reduce blood lipid levels include dietary therapy, exercise therapy and drug therapy. However, dietary therapy or excise therapy is difficult to strictly control and perform, and the therapeutic effect thereof is also limited.

Drugs for reducing lipid levels, developed to date, include bile acid binding resin, cholesterol-lowering drugs such as HMG-CoA reductase inhibitors important in cholesterol biosynthesis, triglyceride-lowering drugs such as fibric acid derivatives and nicotinic acid, etc. However, these drugs were reported to have side effects such as hepatic toxicity, gastrointestinal disorder and carcinogenesis. Thus, there is an urgent need for the development of drugs that can be used to treat hyperlipidemia and related diseases (e.g., atherosclerosis and fatty liver disease) while having less side effects.

As a candidate for such drugs, oxyntomodulin has recently received attention. Oxyntomodulin is produced from pre-glucagon and is a peptide that can bind to both glucagon-like peptide-1 (GLP-1) and glucagon receptor to perform dual function. Because of such characteristics, oxyntomodulin has been studied for various purposes, including the treatment of obesity, hyperlipidemia and fatty liver disease. However, oxyntomodulin has a problem in that it should be administered at a high dose, because it has a short half-life in vivo and the activity thereof is insufficient for use in the treatment of obesity, hyperlipidemia and fatty liver disease.

Accordingly, the present inventors have developed an oxyntomodulin derivative having increased activity compared to native oxyntomodulin and have found that the oxyntomodulin derivative reduced the content and ratio of lipids in blood in a hyperlipidemia-induced hamster model, indicating that the derivative can be effectively used for the treatment of hyperlipidemia diseases, thereby completing the present invention.

DISCLOSURE

Technical Problem

It is an object of the present invention to provide a composition for preventing or treating hyperlipidemia, fatty liver disease or atherosclerosis, which contains an oxyntomodulin derivative as an active ingredient.

Another object of the present invention is to provide a method for treating hyperlipidemia, fatty liver disease or atherosclerosis, the method comprising a step of administering an oxyntomodulin derivative to a subject.

Still another object of the present invention is to provide the use of an oxyntomodulin derivative in the preparation of a medicament for preventing or treating hyperlipidemia, fatty liver disease or atherosclerosis.

Technical Solution

To achieve the above objects, in one aspect, the present invention provides a composition for preventing or treating hyperlipidemia, fatty liver disease or atherosclerosis, which contains an oxyntomodulin derivative as an active ingredient.

As used herein, the term "oxyntomodulin" refers to a peptide produced from pre-glucagon that a precursor of glucagon. In the present invention, oxyntomodulin is meant include native oxyntomodulin and its precursor, analog (derivative), fragment and variant. Preferably, oxyntomodulin has an amino acid sequence of SEQ ID NO: 1 (HSQGT-FTSDYSKYLDSRRAQDFVQWLMNTKRNRNNIA).

As used herein, the term "oxyntomodulin variant" is a peptide that has one or more amino acid residues different from those of the amino acid sequence of native oxyntomodulin and possesses a function of activating GLP-1 and glucagon receptors. The oxyntomodulin variant can be prepared by any one of substitution, addition, deletion, modification, or a combination thereof of some amino acids of native oxyntomodulin.

As used herein, the term "oxyntomodulin derivative" refers to a peptide, peptide derivative or peptide mimic that is prepared by the addition, deletion or substitution of some amino acids of native oxyntomodulin and can activate both GLP-1 receptor and glucagon receptor at a high level compared to the level activated by native oxyntomodulin.

As used herein, the term "oxyntomodulin fragment" refers to a fragment having an addition or deletion of one or more amino acids at the amino or carboxyl terminal end of native oxyntomodulin, in which the added amino acids may also be non-naturally occurring amino acids (e.g., D-type amino acid). Such amino acids have a function of regulating blood glucose levels in vivo.

Methods for preparing the oxyntomodulin variant, derivative and fragment may be used alone or in combination. For example, the present invention includes a peptide that has one or more amino acids different from those of native peptide and deamination of the N-terminal amino acid residues and has a function of activating both GLP-1 receptor and glucagon receptor.

Amino acids mentioned herein are abbreviated according to the nomenclature rules of IUPAC-IUB as follows:
Alanine A;
Arginine R;
Asparagine N;
Aspartic acid D;
Cysteine C;
Glutamic acid E;
Glutamine Q;
Glycine G;
Histidine H;
Isoleucine I;
Leucine L;
Lysine K;
Methionine M;
Phenylalanine F
Proline P;
Serine S;
Threonine T;
Tryptophan W;
Tyrosine Y;
Valine V.

In the present invention, the oxyntomodulin derivative encompasses any peptide that is prepared by the substitution, addition, deletion or post-translational modification (e.g., methylation, acylation, ubiquitination, or intramolecular covalent bonding) of amino acids in the amino acid sequence of SEQ ID NO: 1 and can activate both the glucagon and GLP-1 receptors. Upon substitution or addition of amino acids, not only 20 amino acids commonly found in human proteins, but also atypical or non-naturally occurring amino acids can be used. Commercial sources of atypical amino acids include Sigma-Aldrich, ChemPep Inc., and Genzyme Pharmaceuticals. The peptides including these amino acids and atypical peptide sequences may be synthesized and purchased from commercial suppliers, for example, American Peptide Company or Bachem (USA) or Anygen (Korea).

In a specific embodiment of the present invention, the oxyntomodulin derivative of the present invention is a novel peptide including the amino acid sequence of the following formula 1:

R1-X1-X2-GTFTSD-X3-X4-X5-X6-X7-X8-X9-X10-
X11-X12-X13-X14-X15-X16-X17-X18-X19-
X20-X21-X22-X23-X24-R2 (SEQ ID NO: 54)    [Formula 1]

wherein
R1 is histidine, desamino-histidyl, dimethyl-histidyl (N-dimethyl-histidyl), beta-hydroxyimidazopropionyl, 4-imidazoacetyl, beta-carboxy imidazopropionyl or tyrosine;
X1 is Aib (aminosiobutyric acid), d-alanine, glycine, Sar (N-methylglycine), serine, or d-serine;
X2 is glutamic acid or glutamine;
X3 is leucine or tyrosine;
X4 is serine or alanine;
X5 is lysine or arginine;
X6 is glutamine or tyrosine;
X7 is leucine or methionine;
X8 is aspartic acid or glutamic acid;
X9 is glutamic acid, serine, alpha-methyl-glutamic acid or is deleted;
X10 is glutamine, glutamic acid, lysine, arginine or serine or is deleted;
X11 is alanine, arginine or valine or is deleted;
X12 is alanine, arginine, serine or valine or is deleted;
X13 is lysine, glutamine, arginine or alpha-methyl-glutamic acid or is deleted;
X14 is aspartic acid, glutamic acid or leucine or is deleted;
X15 is phenylalanine or is deleted;
X16 is isoleucine or valine or is deleted;
X17 is alanine, cysteine, glutamic acid, lysine, glutamine or alpha-methyl-glutamic acid or is deleted;
X18 is tryptophan or is deleted;
X19 is alanine, isoleucine, leucine, serine or valine or is deleted;
X20 is alanine, lysine, methionine, glutamine or arginine or is deleted;
X21 is asparagine or is deleted;
X22 is alanine, glycine or threonine or is deleted;
X23 is cysteine or lysine or is deleted;
X24 is a peptide having 2 to 10 amino acids consisting of a combination of alanine, glycine and serine or is deleted; and
R2 is KRNRNNIA (SEQ ID NO: 35), GPSSGAPPPS (SEQ ID NO: 36), GPSSGAPPPSK (SEQ ID NO: 37), HSQGTFTSDYSKYLD (SEQ ID NO: 38), HSQGTFTS-DYSRYLDK (SEQ ID NO: 39), HGEGTFTSDL-SKQMEEEAVK (SEQ ID NO: 40) or is deleted (excluded if the amino acid sequence of formula 1 is identical to that of SEQ ID NO: 1).

In order to increase the activity of wild-type oxyntomodulin for the glucagon receptor and the GLP-1 receptor, the oxyntomodulin derivative of the present invention may be substituted with 4-imidazoacetyl obtained by deletion of the alpha carbon of histidine at position 1 of the amino acid sequence of SEQ ID NO: 1, desamino-histidyl obtained by deletion of the N-terminal amino group, dimethyl-histidyl (N-dimethyl-histidyl) obtained by modification of the N-terminal amino group with two methyl groups, beta-hydroxy imidazopropionyl obtained by substitution of the N-terminal amino group with a hydroxyl group, or beta-carboxy imidazopropionyl obtained by substitution of the N-terminal amino group with a carboxyl group. In addition, the GLP-1 receptor-binding region may be substituted with amino acids that enhance hydrophobic and ionic bonds or a combination thereof. A portion of the oxyntomodulin sequence may be substituted with the amino acid sequence of GLP-1 or Exendin-4 to increase the activity of the GLP-1 receptor.

Further, a portion of the oxyntomodulin sequence may be substituted with a sequence that enhances alpha helix. Preferably, amino acids at positions 10, 14, 16, 20, 24 and 28 of the amino acid sequence of formula 1 may be substituted with amino acids or amino acid derivatives consisting of Tyr(4-Me), Phe, Phe(4-Me), Phe(4-Cl), Phe(4-CN), Phe(4-NO$_2$), Phe(4-NH$_2$), Phg, Pal, Nal, Ala(2-thienyl) and Ala (benzothienyl) that are known to stabilize alpha helix, and the type and number of alpha helix-stabilizing amino acid or amino acid derivatives to be inserted are not limited.

Preferably, amino acids at positions 10 and 14, 12 and 16, 16 and 20, 20 and 24, and 24 and 28 of the amino acid sequence may be also substituted with glutamic acid or lysine so as to form rings, and the number of rings to be inserted is not limited. Most preferably, the oxyntomodulin derivative may have an amino acid sequence selected from among the following formulas 1 to 6.

In a specific embodiment, the oxyntomodulin derivative of the present invention is a novel peptide including the amino acid sequence of the following formula 2, obtained by substitution of the amino acid sequence of oxyntomodulin with that of exendin or GLP-1:

R1-A-R3 (SEQ ID NO: 55)  [Formula 2]

In another specific embodiment, the oxyntomodulin derivative of the present invention is a novel peptide including the amino acid sequence of the following formula 3, which is prepared by linking a portion of the amino acid sequence of oxyntomodulin and a portion of the amino acid sequence of exendin or GLP-1 via a proper amino acid linker:

R1-B-C-R4 (SEQ ID NO: 56)  [Formula 3]

In still another specific embodiment, the oxyntomodulin derivative of the present invention is a novel peptide including the amino acid sequence of the following formula 4, wherein a portion of the amino acid sequence of oxyntomodulin is substituted with an amino acid capable of enhancing the binding affinity to GLP-1 receptor, for example, Leu at position 26 which binds with GLP-1 receptor by hydrophobic interaction is substituted with the hydrophobic residue Ile or Val.

R1-SQGTFTSDYSKYLD-D1-D2-D3-D4-D5-LFVQW-D6-D7-N-D8-R3 (SEQ ID NO: 57)  [Formula 4]

In still another specific embodiment, the oxyntomodulin derivative of the present invention is a novel peptide including the amino acid sequence of the following formula 5, wherein a portion of the amino acid sequence of native oxyntomodulin is deleted, added, or substituted with other amino acids in order to increase the abilities of native oxyntomodulin to activate GLP-1 receptor and glucagon receptor:

R1-E1-QGTFTSDYSKYLD-E2-E3-RA-E4-E5-FV-E6-WLMNT-E7-R5 (SEQ ID NO: 58)  [Formula 5]

In formulas 2 to 5, R1 is as described in formula 1;
A is selected from the group consisting of

SQGTFTSDYSKYLDSRRAQDFVQWLMNT, (SEQ ID NO: 41)

SQGTFTSDYSKYLDEEAVRLFIEWLMNT, (SEQ ID NO: 42)

SQGTFTSDYSKYLDERRAQDFVAWLKNT, (SEQ ID NO: 43)

GQGTFTSDYSRYLEEEAVRLFIEWLKNG, (SEQ ID NO: 44)

GQGTFTSDYSRQMEEEAVRLFIEWLKNG, (SEQ ID NO: 45)

GEGTFTSDLSRQMEEEAVRLFIEWAA, (SEQ ID NO: 46)
and

SQGTFTSDYSRQMEEEAVRLFIEWLMNG; (SEQ ID NO: 47)

B is selected from the group consisting of

SQGTFTSDYSKYLDSRRAQDFVQWLMNT, (SEQ ID NO: 41)

SQGTFTSDYSKYLDEEAVRLFIEWLMNT, (SEQ ID NO: 42)

SQGTFTSDYSKYLDERRAQDFVAWLKNT, (SEQ ID NO: 43)

GQGTFTSDYSRYLEEEAVRLFIEWLKNG, (SEQ ID NO: 44)

GQGTFTSDYSRQMEEEAVRLFIEWLKNG, (SEQ ID NO: 45)

GEGTFTSDLSRQMEEEAVRLFIEWAA, (SEQ ID NO: 46)

SQGTFTSDYSRQMEEEAVRLFIEWLMNG, (SEQ ID NO: 47)

GEGTFTSDLSRQMEEEAVRLFIEW, (SEQ ID NO: 48)
and

SQGTFTSDYSRYLD; (SEQ ID NO: 49)

C is a peptide having 2 to 10 amino acids consisting of a combination of alanine, glycine and serine;
D1 is serine, glutamic acid or arginine;
D2 is arginine, glutamic acid or serine;
D3 is arginine, alanine or valine;
D4 is arginine, valine or serine;
D5 is glutamine, arginine or lysine;
D6 is isoleucine, valine or serine;
D7 is methionine, arginine or glutamine;
D8 is threonine, glycine or alanine;
E1 is serine, Aib, Sar, d-alanine or d-serine;
E2 is serine or glutamic acid;
E3 is arginine or lysine;
E4 is glutamine or lysine;
E5 is aspartic acid or glutamic acid;
E6 is glutamine, cysteine or lysine;
E7 is cysteine or lysine or is deleted;
R3 is KRNRNNIA (SEQ ID NO: 35), GPSSGAPPPS (SEQ ID NO: 36) or GPSSGAPPPSK (SEQ ID NO: 37);

R4 is HSQGTFTSDYSKYLD (SEQ ID NO: 38), HSQGTFTSDYSRYLDK (SEQ ID NO: 39) or HGEGTFTSDLSKQMEEEAVK (SEQ ID NO: 40); and R5 is KRNRNNIA (SEQ ID NO: 35), GPSSGAPPPS (SEQ ID NO: 36) or GPSSGAPPPSK (SEQ ID NO: 37) or is deleted (excluded if the amino acid sequences of formulas 2 to 5 are identical to that of SEQ ID NO: 1).

Preferably, the oxyntomodulin derivative of the present invention may be a novel peptide of the following formula 6:

R1-X1-X2-GTFTSD-X3-X4-X5-X6-X7-X8-X9-X10-X11-X12-X13-X14-X15-X16-X17-X18-X19-X20-X21-X22-X23-X24-R2 (SEQ ID NO: 59) [Formula 6]

wherein R1 is histidine, desamino-histidyl, 4-imidazoacetyl or tyrosine;

X1 is Aib (aminosiobutyric acid), glycine, serine or d-serine;

X2 is glutamic acid or glutamine;

X3 is leucine or tyrosine;

X4 is serine or alanine;

X5 is lysine or arginine;

X6 is glutamine or tyrosine;

X7 is leucine or methionine;

X8 is aspartic acid or glutamic acid;

X9 is glutamic acid or alpha-methyl-glutamic acid or is deleted;

X10 is glutamine, glutamic acid, lysine or arginine or is deleted;

X11 is alanine or arginine or is deleted;

X12 is alanine or valine or is deleted;

X13 is lysine, glutamine, arginine or alpha-methyl-glutamic acid or is deleted;

X14 is aspartic acid, glutamic acid or leucine or is deleted;

X15 is phenylalanine or is deleted;

X16 is isoleucine or valine or is deleted;

X17 is alanine, cysteine, glutamic acid, glutamine or alpha-methyl-glutamic acid or is deleted;

X18 is tryptophan or is deleted;

X19 is alanine, isoleucine, leucine or valine or is deleted;

X20 is alanine, lysine, methionine or arginine or is deleted;

X21 is asparagine or is deleted;

X22 is threonine or is deleted;

X23 is cysteine, lysine or is deleted;

X24 is a peptide having 2 to 10 amino acids consisting of glycine or is deleted; and R2 is KRNRNNIA (SEQ ID NO: 35), GPSSGAPPPS (SEQ ID NO: 36), GPSSGAPPPSK (SEQ ID NO: 37), HSQGTFTSDYSKYLD (SEQ ID NO: 38), HSQGTFTSDYSRYLDK (SEQ ID NO: 39) or HGEGTFTSDLSKQMEEEAVK (SEQ ID NO: 40) or is deleted (excluded if the amino acid sequence of formula 6 is identical to that of SEQ ID NO: 1).

More preferably, the oxyntomodulin derivative of the present invention may be selected from the group consisting of the peptides of SEQ ID NOs: 2 to 34. Even more preferably, the oxyntomodulin derivative of the present invention may be an oxyntomodulin derivative described in Table 1 of Example 2-1.

In an example of the present invention, oxyntomodulin derivatives having the amino acid sequences of SEQ ID NOs: 2 to 34, respectively, were prepared, and it was found that the oxyntomodulin derivatives showed excellent GLP-1 receptor and glucagon receptor activities compared to native oxyntomodulin (Example 2). In other words, it could be seen from the above results that the oxyntomodulin derivative of the present invention exhibited excellent therapeutic effects against hyperlipidemia, fatty liver disease or atherosclerosis by activating the GLP-1 receptor and the glucagon receptor.

The oxyntomodulin derivatives of the present invention are present in the form of conjugates comprising various polymer in order to improve the therapeutic effect and in vivo half-life of the derivatives.

The conjugate of the present invention shows an increase in the duration of effects compared to native oxyntomodulin, and the long-acting conjugates include an oxyntomodulin prepared by the modification, substitution, addition or deletion of the amino acids of native oxyntomodulin, an oxyntomodulin conjugated to a biodegradable polymer such as polyethylene glycol (PEG), an oxyntomodulin conjugated to a polysaccharide such as albumin, antibody, elastin, fibronectin or chitin or to a long-acting protein such as an immunoglobulin fragment, an oxyntomodulin conjugated to fatty acid having the ability of binding to albumin in vivo, or an oxyntomodulin encapsulated in biodegradable nanoparticles, and the type of long-acting conjugate that is used in the present invention is not limited.

Preferably, the conjugate is a conjugate wherein an oxyntomodulin derivative having an amino acid sequence selected from the group consisting of SEQ ID NOs: 2 to 34 is linked to an immunoglobulin Fc region via a non-peptidyl polymer.

The immunoglobulin Fc region is a biodegradable polypeptide that is metabolized in vivo, and thus is safe for use as a carrier for a drug. The immunoglobulin Fc region has a low molecular weight compared to the entire immunoglobulin molecule, and thus is advantageous in terms of the preparation, purification and yield of conjugates. In addition, because the amino acid sequence differs between antibodies, a Fab portion showing high non-homogeneity, and thus the homogeneity of the material can be greatly increased and the possibility of inducing blood antigenicity can also be reduced.

As used herein, the term "immunoglobulin Fc region" refers to a protein that contains the heavy-chain constant region 2 (CH2) and heavy-chain constant region 3 (CH3) of an immunoglobulin, excluding the heavy-chain and light-chain variable regions, the heavy-chain constant region 1 (CH1) and the light-chain constant region 1 (CL1) of the immunoglobulin. It may further include a hinge region at the heavy-chain constant region. Also, the immunoglobulin Fc region of the present invention may be an expanded Fc region including part or all of the heavy-chain constant region 1 (CH1) and/or the light-chain constant region 1 (CL1), except for the heavy-chain and light-chain variable regions, as long as it has an effect that is substantially equal to or better than the native protein. Also, the immunoglobulin Fc region may be a region having a deletion of a portion of a relatively long amino acid sequence corresponding to CH2 and/or CH3. Specifically, the immunoglobulin Fc region of the present invention may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), or 6) a dimer of each domain of the heavy-chain constant regions and the light-chain constant region.

The immunoglobulin Fc region of the present invention includes a native amino acid sequence, and a sequence derivative (mutant) thereof. As used herein, the term "amino acid sequence derivative" refers to a sequence that is different from the native amino acid sequence due to the deletion, insertion, non-conservative or conservative substitution or a combination thereof of one or more amino acid residues of the native amino acid sequence. For example, in the case of an IgG Fc, amino acid residues at positions 214 to 238, 297 to 299, 318 to 322, or 327 to 331, which are known to be important in binding, may be used as suitable sites for modification.

In addition, other various derivatives are possible, including one that has a deletion of a region capable of forming a disulfide bond, or a deletion of some amino acid residues at the N-terminal end of native Fc or an addition of a methionine residue at the N-terminal end of native Fc. Further, to remove effector functions, a deletion may occur in a complement-binding site, such as a C1q-binding site and an ADCC (antibody dependent cell mediated cytotoxicity) site. Techniques of preparing such sequence derivatives of the immunoglobulin Fc region are disclosed in International Patent Publication Nos. WO 97/34631 and WO 96/32478.

Amino acid exchanges in proteins and peptides, which do not generally alter the activity of the proteins or peptides, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In addition, the Fc region may, if necessary, be modified by phosphorylation, sulfation, acrylation, glycosylation, methylation, farnesylation, acetylation, amidation, and the like.

The above-described Fc derivatives show biological activity identical to that of the Fc region of the present invention or have increased structural stability against heat, pH, or the like.

In addition, this Fc region may be obtained from native forms isolated from humans and other animals including cows, goats, pigs, mice, rabbits, hamsters, rats and guinea pigs, or may be recombinants or derivatives thereof, obtained from transformed animal cells or microorganisms. Herein, the Fc region may be obtained from a native immunoglobulin by isolating a whole immunoglobulin from a living human or animal body and treating it with proteinase. When the whole immunoglobulin is treated with papain, it is digested into Fab and Fc regions, and when the whole immunoglobulin is treated with pepsin, it is digested into pF'c and F(ab)$_2$ fragments. Fc or pF'c can be isolated using size exclusion chromatography or the like. Preferably, a human-derived Fc region is a recombinant immunoglobulin Fc region obtained from a microorganism.

In addition, the immunoglobulin Fc region of the present invention may be in the form of having native sugar chains or increased or decreased sugar chains compared to a native form, or may be in a deglycosylated form. The increase, decrease or removal of the immunoglobulin Fc sugar chains may be achieved by conventional methods such as a chemical method, an enzymatic method and a genetic engineering method using a microorganism. The Fc region obtained by removal of sugar chains from Fc shows a significant decrease in binding affinity to the C1q part of the first complement component C1 and a decrease or loss in antibody-dependent cell-mediated cytotoxicity or complement-dependent cytotoxicity, and thus does not induce unnecessary immune responses in vivo. In this regard, an immunoglobulin Fc region in a deglycosylated or aglycosylated form may be more suitable to the object of the present invention as a drug carrier.

As used herein, the term "deglycosylation" refers to enzymatically removing sugar moieties from an Fc region, and the term "aglycosylation" refers to an unglycosylated Fc region produced in a prokaryote, preferably E. coli.

Meanwhile, the immunoglobulin Fc region may be derived from humans or other animals including cows, goats, pigs, mice, rabbits, hamsters, rats and guinea pigs, and preferably from humans.

In addition, the immunoglobulin Fc region may be derived from IgG, IgA, IgD, IgE, IgM, or a combination or hybrid thereof. Preferably, it is derived from IgG or IgM, which are among the most abundant proteins in human blood, and most preferably from IgG, which is known to enhance the half-lives of ligand-binding proteins.

As used herein, the term "combination" means that polypeptides encoding single-chain immunoglobulin Fc regions of the same origin are linked to a single-chain polypeptide of a different origin to form a dimer or multimer. Specifically, a dimer or multimer may be formed from two or more fragments selected from the group consisting of IgG Fc, IgA Fc, IgM Fc, IgD Fc, and IgE Fc fragments.

As used herein, the term "hybrid" means that sequences corresponding to two or more immunoglobulin Fc fragments of different origins are present in a single-chain immunoglobulin Fc region. In the present invention, various forms of hybrid are possible. In other words, a hybrid composed of 1 to 4 domains selected from the group consisting of the CH1, CH2, CH3 and CH4 of IgG Fc, IgM Fc, IgA Fc, IgE Fc and IgD Fc is possible, and it may include a hinge.

Meanwhile, IgG can also be sub-classified into IgG1, IgG2, IgG3 and IgG4, and in the present invention, a combination or hybrid of these subclasses is also possible. Preferably, IgG is the IgG2 ad IgG4 subclass, and most preferably, it is the Fc region of IgG4 that substantially lacks effector functions such as complement-dependent cytotoxicity (CDC).

In other words, the most preferred immunoglobulin Fc region that is used as a drug carrier in the present invention is an Fc region derived from human IgG4. A human-derived Fc region is more preferable than a non-human-derived Fc region, which may act as an antigen in the human body and cause undesirable immune responses such as the production of a new antibody against the antigen.

As used herein, the term "non-peptidyl polymer" refers to a biocompatible polymer including two or more repeating units linked to each other by any covalent bond in place of a peptide bond. In the present invention, the non-peptidyl polymer may be interchangeably used with the non-peptidyl linker.

The non-peptidyl polymer that can be used in the present invention may be selected from the group consisting of polyethylene glycol, polypropylene glycol, an ethylene glycol/propylene glycol copolymer, polyoxyethylated polyol, polyvinyl alcohol, polysaccharides, dextran, polyvinyl ethyl ether, biodegradable polymers such as PLA (poly(lactic acid)) and PLGA (polylactic-glycolic acid), lipid polymers, chitins, hyaluronic acid, and combinations thereof. Preferably, the non-peptidyl polymer is polyethylene glycol. In addition, derivatives thereof known in the art and derivatives that may be easily prepared by a method known in the art are included in the scope of the present invention.

The peptide linker that is used in a fusion protein obtained by a conventional inframe fusion method has drawbacks in that it is easily cleaved by proteinase in vivo, and thus a sufficient effect of increasing the serum half-life of the active drug by a carrier cannot be obtained as expected. However, in the present invention, the polymer having resistance to proteinase can be used to maintain the serum half-life of the peptide, similar to the carrier. Therefore, any non-peptidyl polymer can be used without limitation in the present invention, as long as it is a polymer having the aforementioned function, that is, a polymer having resistance to proteinase in vivo. The non-peptidyl polymer has a molecular weight in the range of 1 to 100 kDa, and preferably 1 to 20 kDa. The non-peptidyl polymer of the present invention, which is linked to the immunoglobulin Fc region, may be one kind of polymer or a combination of different polymers.

The non-peptidyl polymer that is used in the present invention may have a reactive group capable of binding to the immunoglobulin Fc region and the protein drug. The reactive group at both ends of the non-peptidyl polymer is preferably selected from the group consisting of a reactive aldehyde group, a propionaldehyde group, a butyraldehyde group, a maleimide group and a succinimide derivative.

The succinimide derivative may be succinimidyl propionate, hydroxy succinimidyl, succinimidyl carboxymethyl, or succinimidyl carbonate. In particular, when the non-peptidyl polymer has a reactive aldehyde group at both ends thereof, non-specific reactions can be minimized, and a physiologically active polypeptide and an immunoglobulin can be effectively bound to one and the other end of the non-peptidyl polymer, respectively. A final product generated by reductive alkylation with an aldehyde bond is much more stable than that linked by an amide bond. The aldehyde reactive group selectively binds to an N-terminus at a low pH and can form a covalent bond with a lysine residue at a high pH such as pH 9.0.

The reactive groups at both ends of the non-peptidyl polymer may be the same or different. For example, the non-peptidyl polymer may possess a maleimide group at one end, and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the long acting conjugate of the present invention.

The conjugate of the present invention may be one in which one end of the non-peptidyl polymer and the other are linked to an amine group or a thiol group of the immunoglobulin Fc region and the oxyntomodulin derivative, respectively.

The non-peptidyl polymer of the present invention has a functional group at both ends which can be linked to either an immunoglobulin Fc region or a protein drug. The functional groups can be an aldehyde group, a propionaldehyde group, a butyraldehyde group, a maleimide group and a succinimide derivative (i.e., succinimidyl propionate, hydroxy succinimidyl, succinimidyl carboxymethyl, or succinimidyl carbonate), but are not limited thereto.

The reactive groups at both ends of the linker that is the non-peptidyl polymer may be the same or different. For example, the non-peptidyl polymer may have a maleimide group at one end and an aldehyde group, a propionaldehyde group or a butyraldehyde group at the other end. For example, when the non-peptidyl polymer has a reactive aldehyde group at one end and a reactive maleimide group at the other end, non-specific reactions can be minimized, and a physiologically active polypeptide and an immunoglobulin can be effectively bound to both ends of the non-peptidyl polymer. According to an embodiment of the present invention, a conjugate was synthesized by linking oxyntomodulin or its derivative to the immunoglobulin Fc region via a covalent bond using the non-peptidyl polymer PEG including a propionaldehyde group alone or both a maleimide group and an aldehyde group.

The pharmaceutical composition of the present invention can be used for the prevention or treatment of hyperlipidemia, fatty liver disease or atherosclerosis.

As used herein, the term "prevention" refers to all actions that inhibit or delay the development of a target disease. As used herein, the term "prevention" means administering the oxyntomodulin derivative of the present invention to inhibit or delay the development of hyperlipidemia, fatty liver disease or atherosclerosis, which shows an increase in blood total cholesterol and low-density cholesterol levels and a decrease in high-density cholesterol levels.

As used herein, the term "treatment" refers to all actions that, alleviate, ameliorate or relieve the symptoms of the disease developed. As used herein, the term "treatment" means administering the oxyntomodulin derivative of the present invention to alleviate, ameliorate or relieve hyperlipidemia, fatty liver disease or atherosclerosis, which shows an increase in blood total cholesterol and low-density cholesterol levels and a decrease in high-density cholesterol levels.

As used herein, the term "hyperlipidemia" refers to a condition associated with abnormally elevated levels of lipids, such as free cholesterol, cholesterol esters, phospholipids and triglycerides, in blood. Although hyperlipidemia does not show specific symptoms by itself, excessive lipids in blood adhere to the blood vessel walls to reduce the blood vessel size and cause atherosclerosis by inflammatory reactions. For this reason, coronary heart disease, cerebrovascular disease, obstruction of peripheral blood vessels, etc., can occur.

Thus, the pharmaceutical composition of the present invention can be used for the treatment of not only hyperlipidemia, fatty liver disease or atherosclerosis, but also coronary heart disease, cerebrovascular disease, or obstruction of peripheral blood vessels.

As used herein, the term "fatty liver disease" refers to a condition in which the ratio of fats in the weight of the liver is more than 5%. In the present invention, fatty liver diseases include non-alcoholic fatty liver disease (NAFLD), alcoholic fatty liver disease, nutritional fatty liver disease, starvation fatty liver disease, obesity fatty liver disease, diabetic fatty liver disease or steatohepatitis. The non-alcoholic fatty liver disease is meant to include primary and secondary non-alcoholic fatty liver disease, but may preferably be a non-alcoholic fatty liver disease resulting from primary hyperlipidemia, diabetes or obesity.

In addition, in the present invention, non-alcoholic fatty liver disease is meant to include simple steatosis, non-alcoholic steatohepatitis, and liver fibrosis and liver cirrhosis which result from the progression of such diseases.

Atherosclerosis refers to a vascular disease in which atheroma is formed as a result of deposition of cholesterol in the endothelium of blood vessels and proliferation of endothelial cells.

In an example of the present invention, a long-acting oxyntomodulin derivative conjugate was prepared by linking the oxyntomodulin derivative to the immunoglobulin Fc region by a covalent bond using polyethylene glycol, and the prepared conjugate was administered to hamster animal models having hyperlipidemia induced by intake of high-fat diet. As a result, it was shown that the group administered with the long-acting oxyntomodulin derivative conjugate according to the present invention showed a significant decrease in blood triglyceride levels (FIG. 1), a significant decrease in blood total cholesterol levels (FIG. 2), and a significant decrease in blood low-density (LDL) cholesterol levels, compared to the hyperlipidemia-induced animal models. In addition, it was observed that the group administered with the long-acting oxyntomodulin derivative conjugate according to the present invention showed a significant increase in blood high-density (HDL) cholesterol levels (FIG. 4) and a significant increase in the blood HDL-cholesterol/LDL-cholesterol ratio (FIG. 5), compared to the hyperlipidemia-induced animal models.

Further, it could be seen that the long-acting oxyntomodulin derivative conjugate according to the present invention showed a decrease in blood total cholesterol levels (FIG. 6) and a decrease in blood LDL-cholesterol and triglyceride levels (FIG. 7), compared to VICTOZA® that is a commercial long-acting GLP-1 analog. In addition, it could be seen that administration of the long-acting oxyntomodulin derivative conjugate of the present invention showed increases in blood HDL-cholesterol level and the HDL/LDL-cholesterol ratio compared to administration of VICTOZA® (FIGS. 8 and 9). Particularly, a long-acting conjugate of the peptide of SEQ ID NO: 25 with Fc showed significant increases in blood HDL levels and HDL/LDL-cholesterol ratio compared to VICTOZA®.

In other words, the oxyntomodulin derivative according to the present invention reduce blood lipid levels, and thus can be used as an agent for treating hyperlipidemia, fatty liver disease or arteriosclerosis. In addition, the conjugate of the present invention has an excellent ability to activate GLP-1 receptor and glucagon receptor compared to native oxyntomodulin and shows an increased blood half-life in vivo, and thus the activity thereof can be maintained in vivo for an extended period of time.

The oxyntomodulin derivative of the present invention can increase the activity of a factor (Protein kinase or C-ζ or PKC-ζ) regulating the activity of enzymes that are involved in the lipolysis of fats, and increase the expression of a factor (Glut2) that is involved in the lipolysis of fats, thereby treating hyperlipidemia, fatty liver disease or arteriosclerosis, but the scope of the present invention is not limited to the above mechanism of action.

The pharmaceutical composition of the present invention may further comprise a pharmaceutical agent exhibiting preventive or therapeutic effects against hyperlipidemia, fatty liver disease or arteriosclerosis. Specifically, the composition of the present invention may further comprise a pharmaceutical agent known as an agent for treating hyperlipidemia, fatty liver disease or arteriosclerosis in order to administer the pharmaceutical agent in combination with the derivative of the present invention.

Thus, the composition of the present invention may be administered alone or in combination with other drugs in order to prevent or treat hyperlipidemia, fatty liver disease or arteriosclerosis.

As used herein, the term "administration" means introducing a given material into a patient by any appropriate method. The derivative of the present invention may be administered by any general route, as long as it can reach a target tissue. Specifically, the derivative of the present invention may be administered intraperitoneally, intravenously, intramuscularly, subcutaneously, intradermally, orally, locally, intranasally, intrapulmonarily or intrarectally, but is not limited thereto. However, because the peptide is digested when being administered orally, the oral composition is preferably formulated so that the active ingredient is coated or protected from degradation in the stomach. Preferably, the composition of the present invention may be administered in an injectable form. In addition, the pharmaceutical composition of the present invention may be administered using any system capable of delivering the active ingredient to target cells.

The pharmaceutical composition comprising the oxyntomodulin derivative of the present invention may further comprise a pharmaceutically acceptable carrier. For oral administration, pharmaceutically acceptable carriers include a binder, a lubricant, a disintegrant, an excipient, a solubilizer, a dispersing agent, a stabilizer, a suspending agent, a colorant, and a flavorant. For injectable preparations, pharmaceutically acceptable carriers include a buffer, a preservative, an analgesic, a solubilizer, an isotonic agent, and a stabilizer. For topical administration, pharmaceutically acceptable carriers include a base, an excipient, a lubricant, and a preservative.

The pharmaceutical composition of the present invention may be formulated in various dosage forms using the aforementioned pharmaceutically acceptable carriers. For example, for oral administration, the pharmaceutical composition may be formulated into tablets, troches, capsules, elixirs, suspensions, syrups, wafers or the like. For injectable preparations, the pharmaceutical composition may be provided in the form of a unit dosage ampoule or a multiple dosage container. The pharmaceutical composition may also be formulated into solutions, suspensions, tablets, pills, capsules and sustained-release preparations.

Meanwhile, examples of the carrier, excipient and diluent suitable for formulation include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical composition of the present invention may further include fillers, anti-coagulating agents, lubricants, wetting agents, flavors, preservative and the like.

The dose of the pharmaceutical composition of the present invention is determined according to the kind of active ingredient, together with various factors such as the disease to be treated, the route of administration, the patient's age, sex and weight, and the severity of the disease.

The pharmaceutical composition of the present invention has a long in vivo half-life and excellent-potency, and thus the number and frequency of administration of the pharmaceutical composition can be significantly reduced.

In another embodiment, the present invention provides a method for treating hyperlipidemia, fatty liver disease or arteriosclerosis, the method comprising a step of administering the oxyntomodulin derivative of the present invention to a subject.

The above oxyntomodulin, hyperlipidemia, fatty liver disease and arteriosclerosis are as described above.

As used herein, the term "subject" refers to a subject suspected of having hyperlipidemia, fatty liver disease or arteriosclerosis. Specifically, the term means mammals, including humans, rats and domestic animals, which have or are at the risk of developing the above disease. In addition, the subject may be any subject that can be treated by the oxyntomodulin derivative of the present invention.

The therapeutic method of the present invention may comprise administering a pharmaceutically effective amount of the pharmaceutical composition comprising the conjugate. The total daily dose of the composition can be determined through appropriate medical judgment by a physician, and the composition may be administered once or several times. However, in view of the purpose of the present invention, the specific therapeutically effective dose of the composition for any particular patient may vary depending on various factors well known in the medical field, including the kind and degree of response to be achieved, concrete compositions according to whether other agents are used therewith or not, the patient' age, body weight, health condition, sex and diet, the time and route of administration, the secretion rate of the composition, the duration of treatment, other drugs used in combination or coincident with the composition of the present invention, and other factors known in the medical field.

In still another aspect, the present invention provides a method for preparing an oxyntomodulin derivative conjugate.

The preparation method may comprise the steps of: (1) covalently linking a non-peptidyl polymer having a reactive aldehyde, maleimide or succinimide group to the amine or thiol group of an oxyntomodulin derivative peptide; (2) separating the oxyntomodulin derivative peptide, having the non-peptidyl polymer covalently bonded thereto at positions other than the amino terminal end, from the reaction mixture of step (1); and (3) covalently an immunoglobulin Fc region to the other end of the linked non-peptidyl polymer, thereby producing a peptide conjugate comprising the immunoglobulin Fc region and the oxyntomodulin derivative peptide, linked to one and the other end of the non-peptidyl polymer, respectively.

More specifically, the preparation method may comprise the steps of: 1) covalently linking a non-peptidyl polymer, having a reactive aldehyde group and a reactive maleimide group at one and the other end thereof, respectively, to the cysteine residue of an oxyntomodulin derivative; (2) separating the oxyntomodulin derivative, having the non-peptidyl polymer covalently linked to the cysteine residue, from the reaction mixture of step (1); and (3) covalently an immunoglobulin Fc region to the other end of the linked non-peptidyl polymer, thereby producing a peptide conjugate comprising the immunoglobulin Fc region and the oxyntomodulin derivative peptide, linked to one and the other end of the non-peptidyl polymer, respectively.

In still another aspect, the present invention provides the use of the oxyntomodulin derivative in the preparation of a medicament for preventing or treating hyperlipidemia, fatty liver disease or arteriosclerosis.

Advantageous Effects

The oxyntomodulin derivative of the present invention has a high ability to activate GLP-1 receptor and glucagon receptor compared to native oxyntomodulin and exhibits the effects of reducing the blood total cholesterol, low-density cholesterol and triglyceride levels that were increased by high-fat diet, and increasing high-density cholesterol levels and the high-density cholesterol/low-density cholesterol ratio. Thus, the oxyntomodulin derivative of the present invention can be effectively used for the treatment of hyperlipidemia and related diseases.

MODE FOR INVENTION

Figure 1:
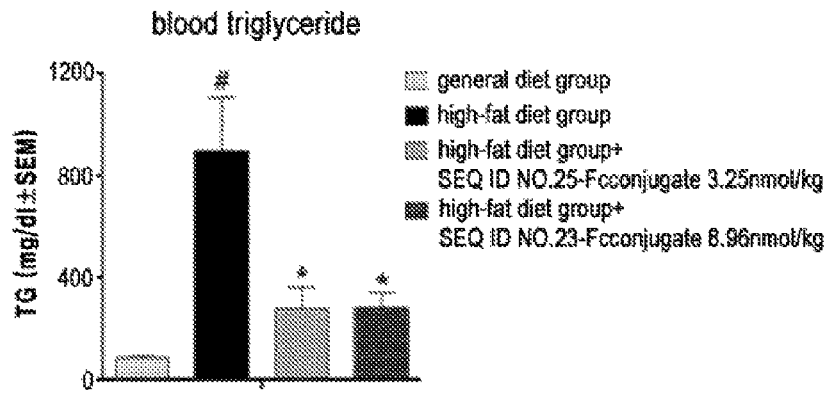
FIG. 1 is a graph showing the change in blood triglyceride levels caused by administration of a long-acting oxyntomodulin derivative to high-fat diet-induced hyperlipidemia hamsters (#: indicates a significant increase compared to a general diet group within a confidence of 99.9% ($p<0.001$); *: indicates a significant decrease compared to a high-fat diet group within a confidence of 99.9% ($p<0.001$).

Hereinafter, the present invention will be described in further detail with reference to examples. It is to be understood, however, that these examples are for illustrative purposes only and are not intended to limit the scope of the present invention.

EXAMPLE 1: Production for Cell Line for In Vitro Activation

Example 1-1: Production of Cell Line Showing cAMP Response to GLP-1

Using a portion corresponding to the ORF (open reading frame) of cDNA (OriGene Technologies, Inc. USA) of the human GLP-1 receptor gene as a template, PCR was performed using reverse and forward primers including a HindIII cleavage site and an EcoRI cleavage site, respectively, thereby obtaining a PCR product.

```
Forward primer:
                              (SEQ ID NO: 50)
5'-CCCGGCCCCCGCGGCCGCTATTCGAAATAC-3'

Reverse primer:
                              (SEQ ID NO: 51)
5'-GAACGGTCCGGAGGACGTCGACTCTTAAGATAG-3'
```

The PCR product was cloned into the known animal cell expression vector x0GC/dhfr, thereby constructing the recombinant vector x0GC/GLP-1R.

The recombinant vector x0GC/GLP-1R was introduced into a CHO DG44 cell line, cultured in DMEM/F12 (10% FBS) medium, using lipofectamine (Invitrogene, USA), to obtain a transformant. The transformant was incubated in a selective medium containing 1 mg/mL G418 and 10 nM methotraxate, and monoclonal cell lines were selected therefrom. Then, a cell line showing a good concentration-dependent cAMP response to GLP-1 was finally selected from the monoclonal cell lines.

Example 1-2: Production of Cell Line Showing cAMP Response to Glucagon

Using a portion corresponding to the ORF (open reading frame) of cDNA (OriGene Technologies, Inc. USA) of the human glucagon receptor gene as a template, PCR was performed using reverse and forward primers including an EcoRI cleavage site and a XhoI cleavage site, respectively, thereby obtaining a PCR product.

```
Forward primer:
                              (SEQ ID NO: 52)
5'-CAGCGACACCGACCGTCCCCCCGTACTTAAGGCC-3'

Reverse Primer:
                              (SEQ ID NO: 53)
5'-CTAACCGACTCTCGGGGAAGACTGAGCTCGCC-3'
```

The PCR product was cloned into the known animal cell expression vector x0GC/dhfr, thereby constructing the recombinant vector x0GC/GCGR.

The recombinant vector x0GC/GCGR was introduced into a CHO DG44 cell line, cultured in DMEM/F12 (10% FBS) medium, using lipofectamine (Invitrogene, USA), to obtain a transformant. The transformant was incubated in a selective medium containing 1 mg/mL G418 and 10 nM methotraxate, and monoclonal cell lines were selected therefrom. Then, a cell line showing a good concentration-dependent cAMP response to glucagon was finally selected from the monoclonal cell lines.

EXAMPLE 2: In Vitro Activity of Oxyntomodulin Derivatives

Example 2-1: Synthesis of Oxyntomodulin Derivatives

In order to measure the in vitro activities of oxyntomodulin derivatives, oxyntomodulin derivatives having the amino acid sequences shown in Table 1 below.

TABLE 1

Oxyntomodulin and oxyntomodulin derivatives

| SEQ ID NOs | Sequences | Note |
|---|---|---|
| SEQ ID NO: 1 | HSQGTFTSDYSKYLDSRRAQDFV QWLMNTKRNRNNIA | |
| SEQ ID NO: 2 | CA-SQGTFTSDYSKYLDEEAVRL FIEWLMNTKRNRNNIA | |
| SEQ ID NO: 3 | CA-SQGTFTSDYSKYLDERRAQD FVAWLKNTGPSSGAPPPS | |
| SEQ ID NO: 4 | CA-GQGTFTSDYSRYLEEEAVRL FIEWLKNGGPSSGAPPPS | |
| SEQ ID NO: 5 | CA-GQGTFTSDYSRQMEEEAVRL FIEWLKNGGPSSGAPPPS | |
| SEQ ID NO: 6 | CA-GEGTFTSDLSRQMEEEAVRL FIEWAAHSQGTFTSDYSKYLD | |
| SEQ ID NO: 7 | CA-SQGTFTSDYSRYLDEEAVRL FIEWLMNTK | |
| SEQ ID NO: 8 | CA-SQGTFTSDLSRQLEEEAVRL FIEWLMNK | |
| SEQ ID NO: 9 | CA-GQGTFTSDYSRYLDEEAVXL FIEWLMNTKRNRNNIA | |
| SEQ ID NO: 10 | CA-SQGTFTSDYSRQMEEEAVRL FIEWLMNGGPSSGAPPPSK | |
| SEQ ID NO: 11 | CA-GEGTFTSDLSRQMEEEAVRL FIEWAAHSQGTFTSDYSRYLDK | |
| SEQ ID NO: 12 | CA-SQGTFTSDYSRYLDGGGHGE GTFTSDLSKQMEEEAVK | |
| SEQ ID NO: 13 | CA-SQGTFTSDYSRYLDXEAVXL FIEWLMNTK | |
| SEQ ID NO: 14 | CA-GQGTFTSDYSRYLDEEAVXL FIXWLMNTKRNRNNIA | |
| SEQ ID NO: 15 | CA-GQGTFTSDYSRYLDEEAVRL FIXWLMNTKRNRNNIA | |
| SEQ ID NO: 16 | CA-SQGTFTSDLSRQLEGGGHSQ GTFTSDLSRQLEK | |
| SEQ ID NO: 17 | CA-SQGTFTSDYSRYLDEEAVRL FIEWIRNTKRNRNNIA | |
| SEQ ID NO: 18 | CA-SQGTFTSDYSRYLDEEAVRL FIEWIRNGGPSSGAPPPSK | |
| SEQ ID NO: 19 | CA-SQGTFTSDYSRYLDEEAVKL FIEWIRNTKRNRNNIA | Ring Formation |
| SEQ ID NO: 20 | CA-SQGTFTSDYSRYLDEEAVKL FIEWIRNGGPSSGAPPPSK | Ring Formation |
| SEQ ID NO: 21 | CA-SQGTFTSDYSRQLEEEAVRL FIEWVRNTKRNRNNIA | |

TABLE 1-continued

Oxyntomodulin and oxyntomodulin derivatives

| SEQ ID NOs | Sequences | Note |
|---|---|---|
| SEQ ID NO: 22 | DA-SQGTFTSDYSKYLDEKRAKE FVQWLMNTK | Ring Formation |
| SEQ ID NO: 23 | HAibQGTFTSDYSKYLDEKRAKE FVCWLMNT | |
| SEQ ID NO: 24 | HAibQGTFTSDYSKYLDEKRAKE FVQWLMNTC | |
| SEQ ID NO: 25 | HAibQGTFTSDYSKYLDEKRAKE FVQWLMNTC | Ring Formation |
| SEQ ID NO: 26 | HAibQGTFTSDYSKYLDEKRAKE FVQWLMNTC | Ring Formation |
| SEQ ID NO: 27 | HAibQGTFTSDYSKYLDEQAAKE FICWLMNT | Ring Formation |
| SEQ ID NO: 28 | HAibQGTFTSDYSKYLDEKRAKE FVQWLMNT | |
| SEQ ID NO: 29 | H(d)SQGTFTSDYSKYLDSRRAQ DFVQWLMNTKRNRNNIA | |
| SEQ ID NO: 30 | CA-SQGTFTSDYSKYLDSRRAQD FVQWLMNTKRNRNNIA | |
| SEQ ID NO: 31 | CA-(d)SQGTFTSDYSKYLDSRR AQDFVQWLMNTKRNRNNIA | |
| SEQ ID NO: 32 | CA-AibQGTFTSDYSKYLDEKRA KEFVQWLMNTC | Ring Formation |
| SEQ ID NO: 33 | HAibQGTFTSDYAKYLDEKRAKE FVQWLMNTC | Ring Formation |
| SEQ ID NO: 34 | YAibQGTFTSDYSKYLDEKRAKE FVQWLMNTC | Ring Formation |

In Table 1 above, the amino acids indicated by the bold letters in each of SEQ ID NOS: 19, 20, 22, 25, 26, 27, 32, 33, and 34, taken together, form a ring, and the amino acids indicated by X mean alpha-methyl-glutamic acid that is a non-native amino acid. In addition, CA indicates 4-imidazoacetyl, DA indicates desamino-histidyl, Aib indicates aminosiobutyric acid, and (d)S indicates d-serine.

Example 2-2: Measurement of In Vitro Activities of Oxyntomodulin Derivatives

In order to measure the effects of anti-obesity peptides, the in vitro activities of cells were measured using the transformants prepared in Examples 1-1 and 1-2.

Each of the transformants was transformed so as to express each of human GLP-1 receptor and glucagon receptor genes in CHO (Chinese hamster ovary) and was suitable for measuring the activities of GLP-1 and glucagon. Thus, the activity of each of the oxyntomodulin derivatives was measured using each of the transformants.

Specifically, each of the transformants was subcultured twice or three times a week, and the cells were dispensed into each well of a 96-well plate at a density of $1 \times 10^5$ cells/well and cultured for 24 hours.

The cultured cells were washed with KRB buffer, suspended in 40 ml of 1 mM IBMX-containing KRB buffer, and then allowed to stand at room temperature for 5 minutes. Each of oxyntomodulin and the oxyntomodulin derivatives (SEQ ID NOs: 2-6, 8, 10-13, 17, 18, 23-25, 27, 28 and 32-34) was serially diluted by five-fold from 1000 nM to 0.02 nM, and 40 ml, of each of the dilutions was added to the cells, which were then incubated in a $CO_2$ incubator at 37° C. for 1 hour. Then, 20 ml of cell lysis buffer was added to lyse the cells, and the concentration of cAMP in each of the cell lysates was measured using a cAMP assay kit (Molecular Device, USA). From the results of the measurement, $EC_{50}$ values were calculated and compared with each other (Table 2).

TABLE 2

Comparison of in vitro activities of GLP-1 receptor and glucagon receptor between oxyntomodulin derivatives

| | $EC_{50}$(nM) | |
|---|---|---|
| SEQ ID NOs | CHO/GLP-1R | CHO/GCGR |
| SEQ ID NO: 1 | 50-210 | 10-43 |
| SEQ ID NO: 2 | 51.8 | 12.8 |
| SEQ ID NO: 3 | >1,000 | 637.7 |
| SEQ ID NO: 4 | 5.5 | >1,000 |
| SEQ ID NO: 5 | 5.9 | >1,000 |
| SEQ ID NO: 6 | 500.1 | >1,000 |
| SEQ ID NO: 8 | 419.6 | >1,000 |
| SEQ ID NO: 10 | >1,000 | >1,000 |
| SEQ ID NO: 11 | >1,000 | >1,000 |
| SEQ ID NO: 12 | >1,000 | >1,000 |
| SEQ ID NO: 13 | >1,000 | >1,000 |
| SEQ ID NO: 17 | 97.9 | >1,000 |
| SEQ ID NO: 18 | 96.3 | >1,000 |
| SEQ ID NO: 23 | 2.46 | 5.8 |
| SEQ ID NO: 24 | 1.43 | 6.95 |
| SEQ ID NO: 25 | 1.9 | 1.3 |
| SEQ ID NO: 27 | 2.8-5.5 | 3.1-5.6 |
| SEQ ID NO: 28 | 3.1 | 0.3 |
| SEQ ID NO: 32 | 41.3 | 17.7 |
| SEQ ID NO: 33 | 2.2 | 80.2 |
| SEQ ID NO: 34 | 12.5 | 1.04 |

As can be seen in Table 2 above, the oxyntomodulin derivatives showed excellent in vitro GLP-1 and glucagon activities compared to the oxyntomodulin of SEQ ID NO:1.

Oxyntomodulin is known to have the effect of treating hyperlipidemia, fatty liver disease or arteriosclerosis by activating GLP-1 receptor and glucagon receptor. The oxyntomodulin derivatives according to the present invention have an excellent activity to activate GLP-1 receptor and glucagon receptor compared to native oxyntomodulin, and thus can be used to treat hyperlipidemia and the fatty liver disease and arteriosclerosis related to hyperlipidemia, in place of native oxyntomodulin.

EXAMPLE 3: Preparation of a Conjugate Comprising an Oxyntomodulin Derivative (SEQ ID NO: 23) with Immunoglobulin Fc (Immunoglobulin Fc-Conjugated Oxyntomodulin Derivative 23)

In order to pegylate a cysteine residue at position 24 of an oxyntomodulin derivative of SEQ ID NO: 23 with MAL-10K-ALD PEG (NOF, Japan), the oxyntomodulin derivative (SEQ ID NO: 23) and MAL-10K-ALD PEG were allowed to react with each other at molar ratio of 1:3 at a protein concentration of 3 mg/ml at room temperature for 3 hours. The reaction was performed in 50 mM Tris buffer (pH 8.0) containing 1M guanidine. After completion of the reaction, the reaction solution was purified using SOURCE S under the following conditions, thereby obtaining an oxyntomodulin mono-pegylated into the cysteine: column: SOURCE S, flow rate: 2.0 ml/min, gradient: A 0→100% 50 min B (A: 20 mM Na-citrate, pH 3.0+45% ethanol, B: A+1M KCl)).

Then, the purified mono-pegylated oxyntomodulin derivative (SEQ ID NO: 23) and immunoglobulin Fc were allowed to react with each other at a molar ratio of 1:5 at a protein concentration of 20 mg/ml at 4° C. for 16 hours. The reaction was performed in 100 mM potassium phosphate buffer (pH 6.0) containing 20 mM SCB as a reducing agent. After completion of the reaction, the reaction solution was purified under the following conditions, thereby obtaining a conjugate comprising the oxyntomodulin derivative (SEQ ID NO: 23) and immunoglobulin: column: SOURCE 15Q, flow rate: 2.0 ml/min, gradient: A 0→4% 1 min, B→20% 80 min B (A: 20 mM Tris-HCl, pH 7.5, B: A+1M NaCl)); source ISO column: SOURCE ISO, flow rate: 2.0 ml/min, gradient: B 0→100% 100 min A, (A: 20 mM Tris-HCl, pH 7.5, B: A+1.1M AS).

EXAMPLE 4: Preparation of a Conjugate Comprising an Oxyntomodulin Derivative (SEQ ID NO: 25) with Immunoglobulin Fc (Immunoglobulin Fc-Conjugated Oxyntomodulin Derivative 25)

In order to pegylate a cysteine residue at position 30 of an oxyntomodulin derivative of SEQ ID NO: 25 with MAL-10K-ALD PEG, the oxyntomodulin derivative (SEQ ID NO: 25) and MAL-10K-ALD PEG were allowed to react with each other at molar ratio of 1:3 at a protein concentration of 3 mg/ml at room temperature for 3 hours. The reaction was performed in 50 mM Tris buffer (pH 8.0) containing 1M guanidine. After completion of the reaction, the reaction solution was purified using SOURCE S under the following conditions, thereby obtaining an oxyntomodulin mono-pegylated into the cysteine: column: SOURCE S, flow rate: 2.0 ml/min, flow rate: A 0→100% 50 min B (A: 20 mM Na-citrate, pH 3.0+45% ethanol, B: A+1M KCl).

Then, the purified mono-pegylated oxyntomodulin derivative (SEQ ID NO: 25) and immunoglobulin Fc were allowed to react with each other at a molar ratio of 1:5 at a protein concentration of 20 mg/ml at 4° C. for 16 hours. The reaction was performed in 100 mM potassium phosphate buffer (pH 6.0) containing 20 mM SCB as a reducing agent. After completion of the reaction, the reaction solution was purified under the following conditions, thereby obtaining a conjugate comprising the oxyntomodulin derivative (SEQ ID NO: 25) and immunoglobulin: SOURCE 15Q column: SOURCE 15Q, flow rate: 2.0 ml/min, flow rate: A 0→4% 1 min B→20% 80 min B (A: 20 mM Tris-HCl, pH 7.5, B: A+1M NaCl); and Source ISO column: SOURCE ISO, flow rate: 2.0 ml/min, flow rate: B 0→100% 100 min A (A: 20 mM Tris-HCl, pH 7.5, B: A+1.1M AS).

EXAMPLE 5: Effect of Long-Acting Oxyntomodulin on Reduction in Lipid in Hyperlipidemia Model Hamsters Example 5-1: Grouping of Test Animals 8 week-old male hamsters (Golden Syrian hamsters, 120-130 g) were purchased from Vital River China. It is known that hamsters show blood lipid profiles similar to humans, unlike other rodents, and are sensitive to high-fat diets.

The animals were allowed access to a sterilized high-fat diet (Purina 5001 containing 11.5% maize oil, 11.5% coconut oil, 0.5% cholesterol, and 0.25% deoxycholate; Dyets, Bethlehem, Pa.) or a standard rodent diet (low fat, 2018; Harlan Teklad, Madison, Wis.). A normal diet group was allowed access to filtered and UV-sterilized tap water, and a high-fat diet group was allowed access to water containing 10% fructose. The animals were kept in a breeding chamber satisfying GLP standards under a 12-hr light/12-hr dark cycle (lighting: am 6 to pm 6), and all the experimental procedures were performed according to the standard guideline for animal experiments. Drug administration was started after 3 weeks of hyperlipidemia induction, and the animals were divided into four groups (n=6) as shown in Table 3 below.

TABLE 3

| Groups | Drugs administered | Method of administration |
|---|---|---|
| Normal group | Vehicle (DPBS) | Administered subcutaneously once a week |
| Hyperlipidemia-induced group | Vehicle (DPBS) 3.25 nmol/kg of SEQ ID NO: 25-Fc conjugate 8.96 nmo/kg of SEQ ID NO: 23-Fc conjugate | |

Specifically, group 1 (normal group) was fed with a normal feed and administered subcutaneously with 5 ml/kg of Dulbecco's phosphate buffered saline (DPBS, Sigma) once or more a week.

Group 2 (hyperlipidemia-induced group) was fed with a high-fat diet to induce hyperlipidemia, and then administered subcutaneously with 5 ml/kg of Dulbecco's phosphate buffered saline (DPBS, Sigma) once or more a week.

Group 3 (hyperlipidemia-induced group+group administered with 3.25 nmol/kg of SEQ ID NO: 25-Fc conjugate) was fed with a high-fat diet to induce hyperlipidemia, and then administered with 3.25 nmol/kg of the SEQ ID NO: 25-Fc conjugate (prepared in Example 4) once a week at an injection dose of 5 ml/kg.

Group 4 (hyperlipidemia-induced group+group administered with 8.96 nmol/kg of SEQ ID NO: 23-Fc conjugate) was fed with a high-fat diet to induce hyperlipidemia, and then administered with 8.96 nmol/kg of the SEQ ID NO: 23-Fc conjugate (prepared in Example 3) once a week at an injection dose of 5 ml/kg.

Saline or the drug was administered into each group (n=6) for 2 weeks, and then the effects thereof on a reduction in lipid levels were analyzed.

Example 5-2: Analysis of Effect of Long-Acting Oxyntomodulin Derivative Conjugate on Reduction in Lipid Levels In order to examine the effect of the long-acting oxyntomodulin derivative conjugate on a reduction in lipid levels in hamsters, the following experiment was performed.

Blood was collected from the hamsters which were administered or not administered with the long-acting oxyntomodulin derivative as described in Example 5-1, and the lipid levels of the blood were analyzed using HITACHI 7020. The results of the analysis are shown in FIGS. 1 to 5.

Figure 3:
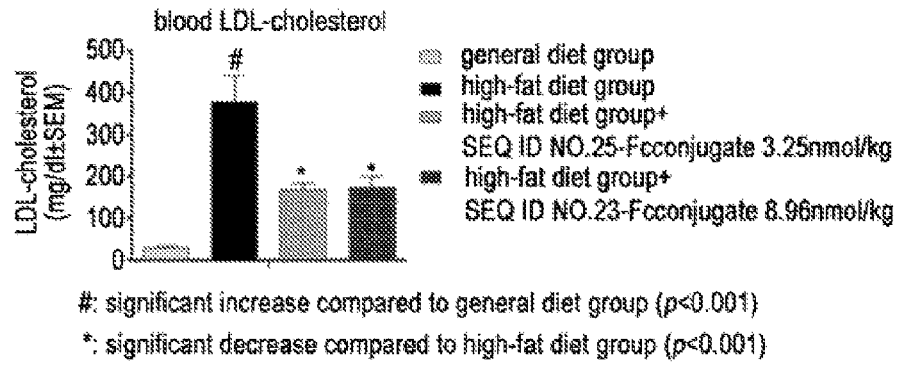
FIG. 3 is a graph showing the change in blood LDL-cholesterol levels caused by administration of a long-acting oxyntomodulin derivative to high-fat diet-induced hyperlipidemia hamsters (#: indicates a significant increase compared to a general diet group within a confidence of 99.9% ($p<0.001$);*: indicates a significant decrease compared to a high-fat diet group within a confidence of 99.9% ($p<0.001$).
Figure 4:
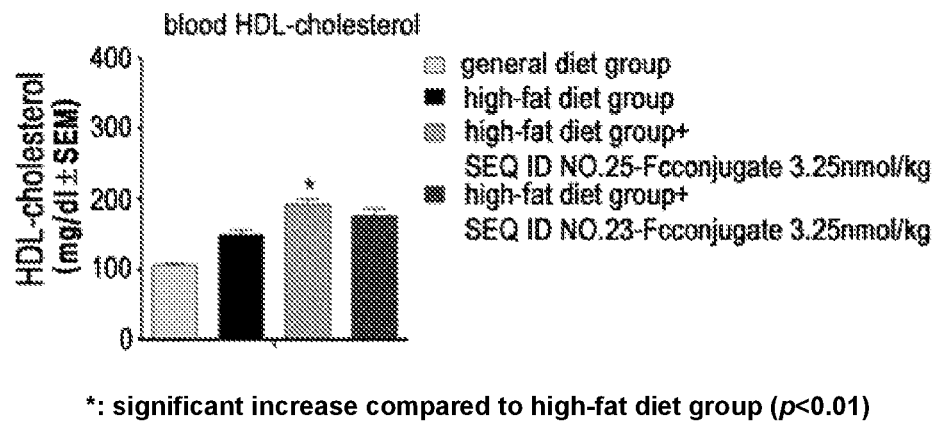
FIG. 4 is a graph showing the change in blood HDL-cholesterol levels caused by administration of a long-acting oxyntomodulin derivative to high-fat diet-induced hyperlipidemia hamsters (*: indicates a significant increase compared to a high-fat diet group within a confidence of 99% ($p<0.01$).
Figure 5:
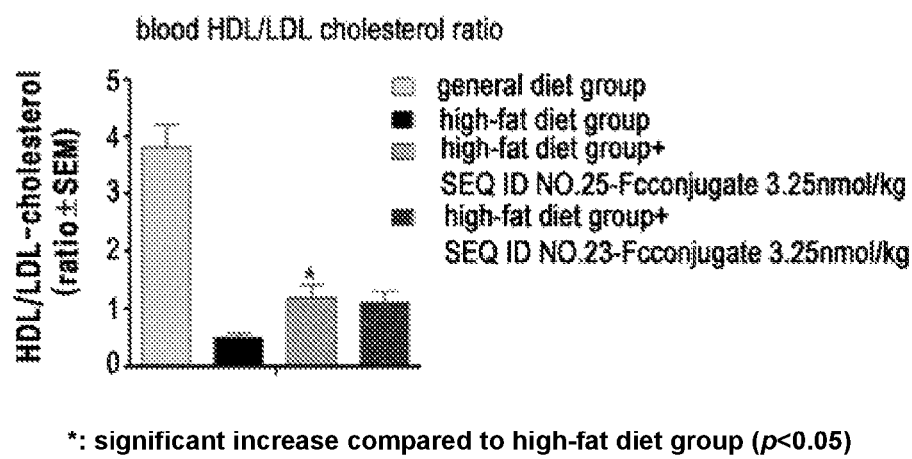
FIG. 5 is a graph showing the change in blood HDL/LDL-cholesterol levels caused by administration of a long-acting oxyntomodulin derivative to high-fat diet-induced hyperlipidemia hamsters (*: shows a significant increase compared to a high-fat diet group within a confidence of 95% ($p<0.05$).

FIGS. 1 to 5 show the change in blood triglyceride levels (FIG. 1), the change in blood total cholesterol levels (FIG. 2), the change in LDL-cholesterol levels (FIG. 3), blood HDL-cholesterol levels (FIG. 4), and the change in the blood HDL/LDL-cholesterol ratio (FIG. 5). The obtained results were statistically processed, and the mean values and the standard deviations of the mean values were calculated. In the verification of significance between the groups (n=6), data were statistically processed using Dunnett's test of one-way ANOVA, and a value of $p<0.05$ was considered statistically significant.

Specifically, in the results of measurement of blood triglyceride levels, it was seen that, in the case of hamsters fed with a high-fat diet, the triglyceride levels were significantly increased, but when the long-acting oxyntomodulin derivative (SEQ ID NO: 25-Fc conjugate or SEQ ID NO: 23-Fc conjugate) was administered into the hamsters, the triglyceride levels were significantly decreased (FIG. 1).

Figure 2:
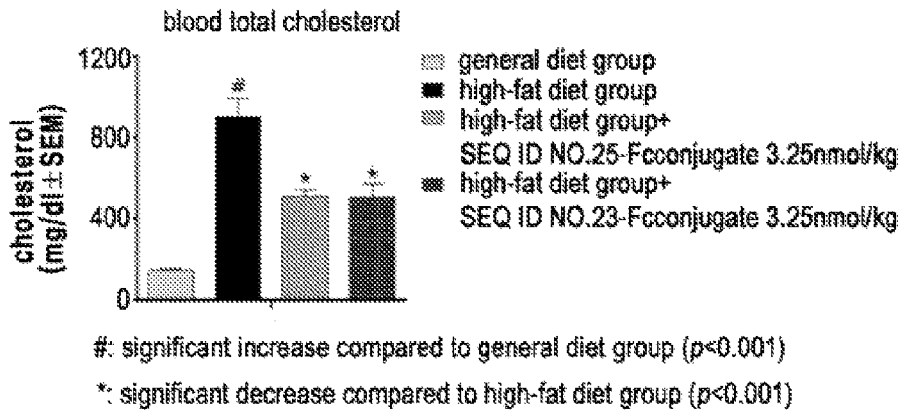
FIG. 2 is a graph showing the change in blood total cholesterol levels caused by administration of a long-acting oxyntomodulin derivative to high-fat diet-induced hyperlipidemia hamsters (#: indicates a significant increase compared to a general diet group within a confidence of 99.9% ($p<0.001$);*: indicates a significant decrease compared to a high-fat diet group within a confidence of 99.9% ($p<0.001$).

In the results of measurement of blood total cholesterol levels, it was seen that, in the case of hamsters fed with a high-fat diet, the blood total cholesterol levels were significantly increased, but when the long-acting oxyntomodulin derivative (SEQ ID NO: 25-Fc conjugate or SEQ ID NO: 23-Fc conjugate) was administered into the hamsters, the blood total cholesterol levels were significantly decreased (FIG. 2).

In the results of measurement of blood LDL-cholesterol levels, it was seen that, in the case of hamsters fed with a high-fat diet, the blood LDL-cholesterol levels were significantly increased, but when the long-acting oxyntomodulin derivative (SEQ ID NO: 25-Fc conjugate or SEQ ID NO: 23-Fc conjugate) was administered into the hamsters, the blood LDL-cholesterol cholesterol levels were significantly decreased (FIG. 3).

In the results of measurement of blood HDL-cholesterol levels, the group administered with the SEQ ID NO: 25-Fc conjugate or the SEQ ID NO: 23-Fc conjugate showed a significant increase in the blood HDL-cholesterol levels compared to the high-fat diet hamster group (FIG. 4).

In the results of measurement of blood HDL/LDL-cholesterol levels, the group administered with the SEQ ID NO: 25-Fc conjugate or the SEQ ID NO: 23-Fc conjugate showed a significant increase in the blood HDL/LDL-cholesterol ratio compared to the high-fat diet hamster group (FIG. 5).

From the above results, it could be seen that the inventive oxyntomodulin derivative conjugate comprising the immunoglobulin Fc region covalently linked to the oxyntomodulin derivative by PEG prevents the accumulation of blood triglyceride and low-density (LDL) cholesterol, and thus can be effectively used for the treatment of hyperlipidemia or related fatty liver disease or arteriosclerosis.

EXAMPLE 6: Analysis of Effects of Known Long-Acting GLP-1 Analog and Long-Acting Oxyntomodulin Derivative Conjugate VICTOZA® is a long-acting glucagon-like peptide-1, GLP-1 analog which is currently marketed as an agent for treating diabetes and is known to have the effects of treating obesity and increasing HDL cholesterol levels.

The effect of reducing lipid levels was compared between the oxyntomodulin derivative conjugate and known VICTOZA®.

As described in Example 5, hamsters were divided into a normal hamster group and hamster groups fed with a high-fat diet. The normal hamster group was administered subcutaneously with 5 ml/kg of DPBS once or more a week. The hamster groups fed with high-fat diet were divided into a group administered subcutaneously with 5 ml/kg of DPBS once or more a week, a group administered subcutaneously with 35.5 nmol/kg of VICTOZA® once or more a week, a group administered subcutaneously with 3.25 nmol/kg of the SEQ ID NO: 25-Fc conjugate, and a group administered subcutaneously with 8.96 nmol/kg of the SEQ ID NO:23-Fc conjugate, and the blood lipid levels of the groups were analyzed.

Figure 6:
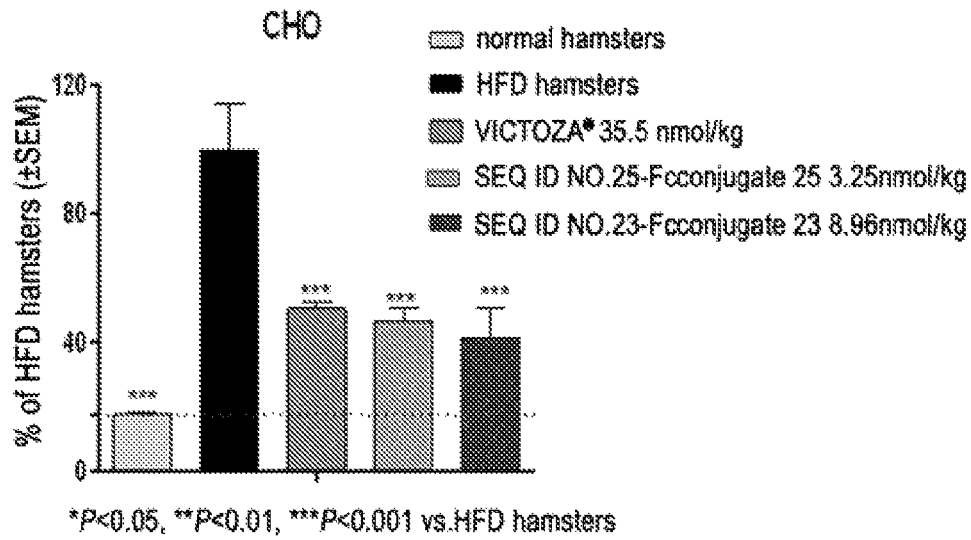
FIG. 6 is a graph showing the change in blood total cholesterol levels caused by administration of VICTOZA® or a long-acting oxyntomodulin derivative to high-fat diet-induced hyperlipidemia hamsters (***: indicates a significant decrease compared to a high-fat diet group within a confidence of 99.9% ($p<0.001$).
Figure 7:
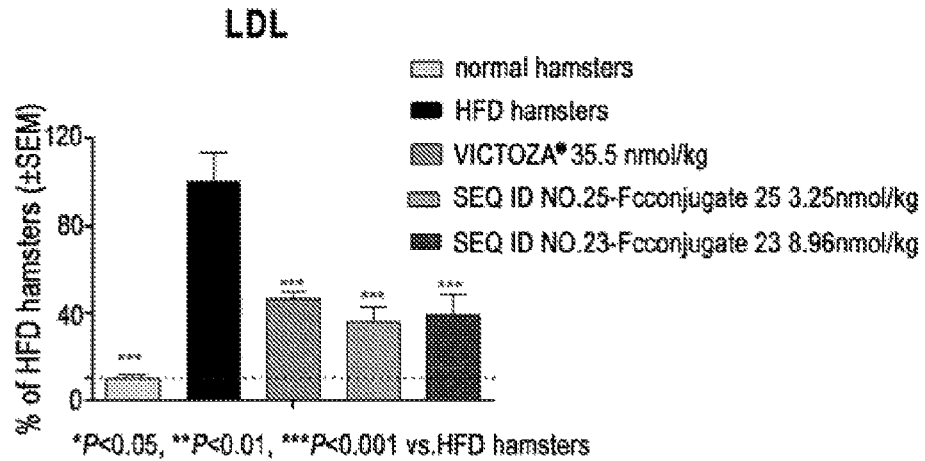
FIG. 7 is a graph showing the change in blood LDL-cholesterol levels caused by administration of VICTOZA® or a long-acting oxyntomodulin derivative to high-fat diet-induced hyperlipidemia hamsters (***: indicates a significant decrease compared to a high-fat diet group within a confidence of 99.9% ($p<0.001$).

As a result, it could be seen that administration of the inventive long-acting oxyntomodulin derivative conjugate (SEQ ID NO: 25-Fc conjugate or SEQ ID NO: 23-Fe conjugate) showed a decrease in blood total cholesterol levels (FIG. 6) and a decrease in blood LDL-cholesterol level (FIG. 7) compared to administration of commercial VICTOZA®.

Figure 8:
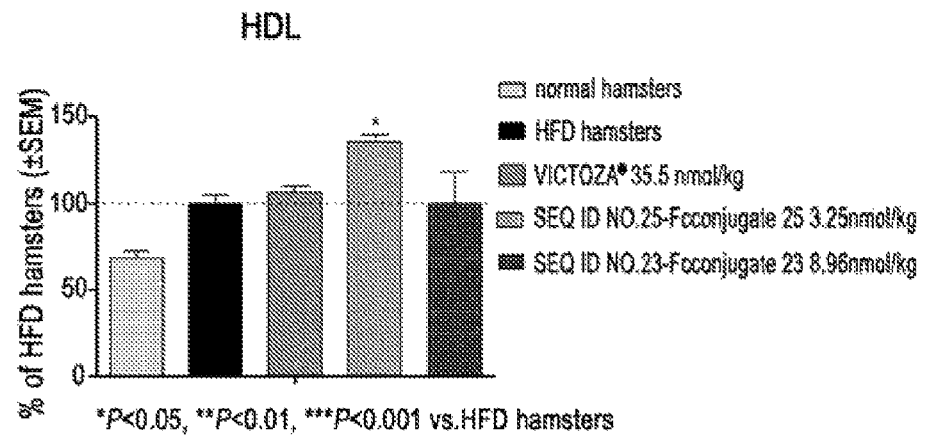
FIG. 8 is a graph showing the change in blood HDL-cholesterol levels caused by administration of VICTOZA® or a long-acting oxyntomodulin derivative to high-fat diet-induced hyperlipidemia hamsters (*: indicates a significant decrease compared to a high-fat diet group within a confidence of 95% ($p<0.05$).
Figure 9:
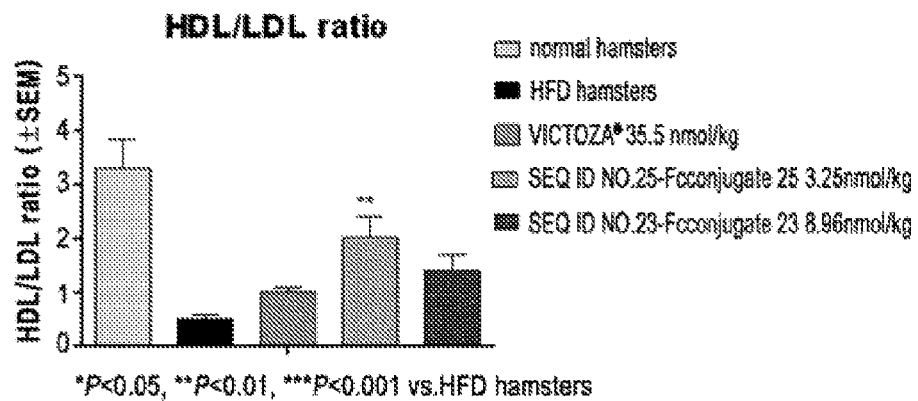
FIG. 9 is a graph showing the change in blood HDL/LDL-cholesterol levels caused by administration of VICTOZA® or a long-acting oxyntomodulin derivative to high-fat diet-induced hyperlipidemia hamsters (**: indicates a significant decrease compared to a high-fat diet group within a confidence of 99% ($p<0.01$).
Figure 10:
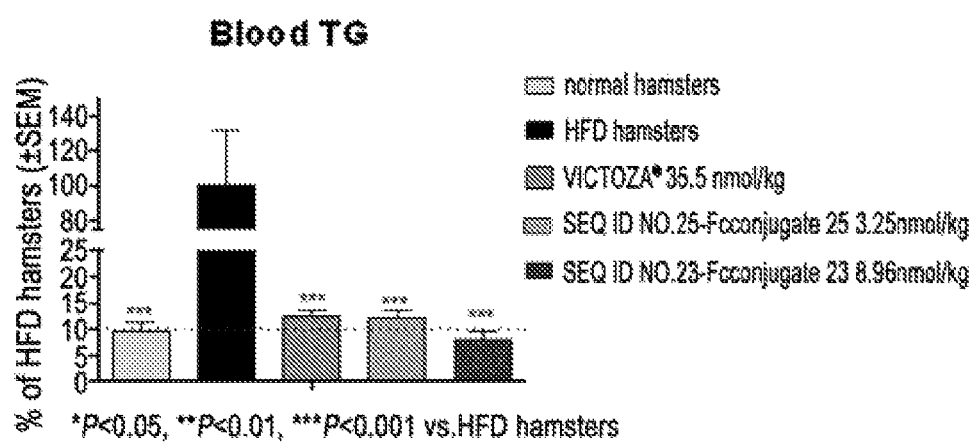
FIG. 10 is a graph showing the change in blood triglyceride levels caused by administration of VICTOZA® or a long-acting oxyntomodulin derivative to high-fat diet-induced hyperlipidemia hamsters (***: indicates a significant decrease compared to a high-fat diet group within a confidence of 99.9% ($p<0.001$).

In addition, it could be seen that administration of the inventive long-acting oxyntomodulin derivative conjugate (SEQ ID NO: 25-Fe conjugate or SEQ ID NO: 23-Fe conjugate) showed increases in blood HDL-cholesterol levels and the HDL/LDL-cholesterol ratio compared to administration of VICTOZA® (FIGS. 8 and 9). Particularly, the long-acting SEQ ID NO: 25-Fc conjugate showed significant increases in blood HDL-cholesterol levels and the HDL/LDL-cholesterol ratio compared to VICTOZA®.

In addition, administration of the inventive long-acting oxyntomodulin derivative conjugate (SEQ ID NO: 25-Fc conjugate or SEQ ID NO: 23-Fe conjugate) showed a decrease in blood triglyceride levels compared to administration of VICTOZA®.

From the above results, it can be seen that the long-acting oxyntomodulin derivative conjugate of the present invention exhibits a lipid-lowering effect that is equal to or higher than that of known VICTOZA®, and thus the conjugate can be effectively used as an agent for treating hyperlipidemia, fatty liver disease or arteriosclerosis.

The invention claimed is:

1. A method for treating hyperlipidemia, fatty liver disease, atherosclerosis, or arteriosclerosis, comprising administering an oxyntomodulin derivative conjugate to a subject in need thereof, wherein the oxyntomodulin derivative conjugate comprises: an oxyntomodulin derivative comprising the amino acid sequence of SEQ ID NO: 24, 25, or 26; an immunoglobulin Fc region; and a non-peptidyl polymer, wherein the non-peptidyl polymer covalently links the oxyntomodulin derivative and the immunoglobulin Fc region.

2. The method of claim 1, wherein the oxyntomodulin derivative comprises the amino acid sequence of SEQ ID NO: 24.

3. The method of claim 1, wherein the oxyntomodulin derivative comprises the amino acid sequence of SEQ ID NO: 25.

4. The method of claim 1, wherein the oxyntomodulin derivative comprises the amino acid sequence of SEQ ID NO: 26.

5. The method of claim 1, wherein the non-peptidyl polymer is polyethylene glycol, polypropylene glycol, an ethylene glycol/propylene glycol copolymer, a polyoxyethylated polyol, polyvinyl alcohol, a polysaccharide, polyvinyl ethyl ether, polylactic acid, polylactic-glycolic acid, a lipid polymer, hyaluronic acid, or a combination thereof.

6. The method of claim 5, wherein the non-peptidyl polymer is polyethylene glycol.

7. The method of claim 5, wherein the polysaccharide is dextran, a chitin, or a combination thereof.

8. The method of claim 1, wherein one end of the non-peptidyl polymer is linked to an amine group or a thiol group of the immunoglobulin Fc region and the other end of the non-peptidyl polymer is linked to an amine group or a thiol group of the oxyntomodulin derivative.

9. The method of claim 1, wherein the fatty liver disease is non-alcoholic fatty liver disease, alcoholic fatty liver disease, nutritional fatty liver disease, starvation fatty liver disease, or steatohepatitis.

10. The method of claim 9, wherein the non-alcoholic fatty liver disease is simple steatosis, non-alcoholic steatohepatitis, liver fibrosis or liver cirrhosis.

11. A method for treating hyperlipidemia, fatty liver disease, atherosclerosis, or arteriosclerosis, comprising administering an oxyntomodulin derivative conjugate to a subject in need thereof, wherein the oxyntomodulin derivative conjugate comprises: an oxyntomodulin derivative comprising the amino acid sequence of SEQ ID NO: 28; an immunoglobulin Fc region; and a non-peptidyl polymer, wherein the non-peptidyl polymer is polyethylene glycol, polypropylene glycol, an ethylene glycol/propylene glycol copolymer, a polyoxyethylated polyol, polyvinyl alcohol, polyvinyl ethyl ether, polylactic acid, polylactic-glycolic acid, a lipid polymer, hyaluronic acid, or a combination thereof, and wherein the non-peptidyl polymer covalently links the oxyntomodulin derivative and the immunoglobulin Fc region.

12. The method of claim 11, wherein the non-peptidyl polymer is polyethylene glycol.

13. The method of claim 11, wherein one end of the non-peptidyl polymer is linked to an amine group or a thiol group of the immunoglobulin Fc region and the other end of the non-peptidyl polymer is linked to an amine group or a thiol group of the oxyntomodulin derivative.

14. The method of claim 11, wherein the fatty liver disease is non-alcoholic fatty liver disease, alcoholic fatty liver disease, nutritional fatty liver disease, starvation fatty liver disease, or steatohepatitis.

15. The method of claim 14, wherein the non-alcoholic fatty liver disease is simple steatosis, non-alcoholic steatohepatitis, liver fibrosis or liver cirrhosis.

* * * * *

SEQUENCE LISTING

```
<160> NUMBER OF SEQ ID NOS: 59

<210> SEQ ID NO 1
<211> LENGTH: 37
<212> TYPE: PRT
<213> ORGANISM: Homo sapiens
<220> FEATURE:
<221> NAME/KEY: MISC_FEATURE
<222> LOCATION: (1)..(37)
<223> OTHER INFORMATION: Oxyntomodulin

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```

```
<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 2

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 3

His Ser Gln Gly Thr Phe Thr Ser Asp Tyr Ser Lys Tyr Leu Asp Glu
1               5                   10                  15

Arg Arg Ala Gln Asp Phe Val Ala Trp Leu Lys Asn Thr Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 4

His Gly Gln Gly Thr Phe Thr Ser Asp Tyr Ser Arg Tyr Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
```

```
<220> FEATURE:
<221> NAME/KEY: MOD_RES
<222> LOCATION: (1)..(1)
<223> OTHER INFORMATION: 4-imidazoacetyl

<400> SEQUENCE: 5

His Gly Gln Gly Thr Phe Thr Ser Asp Tyr Ser Arg Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 6

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Lys Tyr Leu Asp
        35                  40

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 7

His Ser Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys
            20                  25                  30

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      oxyntomodulin derivative peptide
<220> FEATURE:
<221> NAME/KEY: MOD_RES
<222> LOCATION: (1)..(1)
<223> OTHER INFORMATION: 4-imidazoacetyl
```

```
<400> SEQUENCE: 8

His Ser Gln Gly Thr Phe Thr Ser Asp Leu Ser Arg Gln Leu Glu Glu
1               5                   10                  15

Glu Ala Val Arg Leu Phe Ile Glu Trp Leu Met Asn Lys
            20                  25

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-glutamic acid

<400> SEQUENCE: 9

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 10

His Ser Gln Gly Thr Phe Thr Ser Asp Tyr Ser Arg Gln Met Glu Glu
1               5                   10                  15

Glu Ala Val Arg Leu Phe Ile Glu Trp Leu Met Asn Gly Gly Pro Ser
            20                  25                  30

Ser Gly Ala Pro Pro Pro Ser Lys
        35                  40

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl
```

```
<400> SEQUENCE: 11

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Arg Tyr Leu Asp Lys
        35                  40

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 12

His Ser Gln Gly Thr Phe Thr Ser Asp Tyr Ser Arg Tyr Leu Asp Gly
1               5                   10                  15

Gly Gly His Gly Glu Gly Thr Phe Thr Ser Asp Leu Ser Lys Gln Met
            20                  25                  30

Glu Glu Glu Ala Val Lys
        35

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (16)..(16)
<223> OTHER INFORMATION: Alpha-methyl-glutamic acid
<220> FEATURE:
<221> NAME/KEY: MOD_RES
<222> LOCATION: (20)..(20)
<223> OTHER INFORMATION: Alpha-methyl-glutamic acid

<400> SEQUENCE: 13

His Ser Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys
            20                  25                  30

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl
```

```
<220> FEATURE:
<221> NAME/KEY: MOD_RES
<222> LOCATION: (20)..(20)
<223> OTHER INFORMATION: Alpha-methyl-glutamic acid
<220> FEATURE:
<221> NAME/KEY: MOD_RES
<222> LOCATION: (24)..(24)
<223> OTHER INFORMATION: Alpha-methyl-glutamic acid

<400> SEQUENCE: 14

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (24)..(24)
<223> OTHER INFORMATION: Alpha-methyl-glutamic acid

<400> SEQUENCE: 15

His Gly Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 16

His Ser Gln Gly Thr Phe Thr Ser Asp Leu Ser Arg Gln Leu Glu Gly
1               5                   10                  15

Gly Gly His Ser Gln Gly Thr Phe Thr Ser Asp Leu Ser Arg Gln Leu
            20                  25                  30

Glu Lys

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
```

```
<220> FEATURE:
<221> NAME/KEY: MOD_RES
<222> LOCATION: (1)..(1)
<223> OTHER INFORMATION: 4-imidazoacetyl

<400> SEQUENCE: 17

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Thr Lys Arg Asn
            20                  25                  30

Arg Asn Asn Ile Ala
            35

<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 18

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Gly Gly Pro Ser
            20                  25                  30

Ser Gly Ala Pro Pro Pro Ser Lys
            35                  40

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 19

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Thr Lys Arg Asn
            20                  25                  30

Arg Asn Asn Ile Ala
            35

<210> SEQ ID NO 20
<211> LENGTH: 40
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
```

```
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 20

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Gly Gly Pro Ser
            20                  25                  30

Ser Gly Ala Pro Pro Pro Ser Lys
        35                  40

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 21

His Ser Gln Gly Thr Phe Thr Ser Asp Tyr Ser Arg Gln Leu Glu Glu
1               5                   10                  15

Glu Ala Val Arg Leu Phe Ile Glu Trp Val Arg Asn Thr Lys Arg Asn
            20                  25                  30

Arg Asn Asn Ile Ala
        35

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: Desamino-histidyl
<220> FEATURE:
<221> NAME/KEY: MISC_FEATURE
<222> LOCATION: (16)..(20)
<223> OTHER INFORMATION: Ring formation between residues

<400> SEQUENCE: 22

His Ser Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Lys
            20                  25                  30

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      oxyntomodulin derivative peptide
```

```
<220> FEATURE:
<221> NAME/KEY: MOD_RES
<222> LOCATION: (2)..(2)
<223> OTHER INFORMATION: Aib

<400> SEQUENCE: 23

His Xaa Gln Gly Thr Phe Thr Ser Asp Tyr Ser Lys Tyr Leu Asp Glu
1               5                   10                  15

Lys Arg Ala Lys Glu Phe Val Cys Trp Leu Met Asn Thr
            20                  25

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (2)..(2)
<223> OTHER INFORMATION: Aib

<400> SEQUENCE: 24

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 25

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (12)..(16)
<223> OTHER INFORMATION: Ring formation between residues
```

```
<400> SEQUENCE: 26

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      oxyntomodulin derivative peptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 27

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      oxyntomodulin derivative peptide
<220> FEATURE:
<221> NAME/KEY: MOD_RES
<222> LOCATION: (2)..(2)
<223> OTHER INFORMATION: Aib

<400> SEQUENCE: 28

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr
            20                  25

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (2)..(2)
<223> OTHER INFORMATION: D-Ser

<400> SEQUENCE: 29

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35
```

```
<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl

<400> SEQUENCE: 30

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: D-Ser

<400> SEQUENCE: 31

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 32

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30
```

```
<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 33

His Xaa Gln Gly Thr Phe Thr Ser Asp Tyr Ala Lys Tyr Leu Asp Glu
1               5                   10                  15

Lys Arg Ala Lys Glu Phe Val Gln Trp Leu Met Asn Thr Cys
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 34

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      group R2 peptide

<400> SEQUENCE: 35

Lys Arg Asn Arg Asn Asn Ile Ala
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      group R2 peptide

<400> SEQUENCE: 36

Gly Pro Ser Ser Gly Ala Pro Pro Pro Ser
1               5                   10
```

-continued

```
<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      group R2 peptide

<400> SEQUENCE: 37

Gly Pro Ser Ser Gly Ala Pro Pro Pro Ser Lys
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      group R2 peptide

<400> SEQUENCE: 38

His Ser Gln Gly Thr Phe Thr Ser Asp Tyr Ser Lys Tyr Leu Asp
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      group R2 peptide

<400> SEQUENCE: 39

His Ser Gln Gly Thr Phe Thr Ser Asp Tyr Ser Arg Tyr Leu Asp Lys
1               5                   10                  15

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      group R2 peptide

<400> SEQUENCE: 40

His Gly Glu Gly Thr Phe Thr Ser Asp Leu Ser Lys Gln Met Glu Glu
1               5                   10                  15

Glu Ala Val Lys
            20

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      group A or B peptide

<400> SEQUENCE: 41

Ser Gln Gly Thr Phe Thr Ser Asp Tyr Ser Lys Tyr Leu Asp Ser Arg
1               5                   10                  15

Arg Ala Gln Asp Phe Val Gln Trp Leu Met Asn Thr
            20                  25
```

```
<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      group A or B peptide

<400> SEQUENCE: 42

Ser Gln Gly Thr Phe Thr Ser Asp Tyr Ser Lys Tyr Leu Asp Glu Glu
1               5                   10                  15

Ala Val Arg Leu Phe Ile Glu Trp Leu Met Asn Thr
            20                  25

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      group A or B peptide

<400> SEQUENCE: 43

Ser Gln Gly Thr Phe Thr Ser Asp Tyr Ser Lys Tyr Leu Asp Glu Arg
1               5                   10                  15

Arg Ala Gln Asp Phe Val Ala Trp Leu Lys Asn Thr
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      group A or B peptide

<400> SEQUENCE: 44

Gly Gln Gly Thr Phe Thr Ser Asp Tyr Ser Arg Tyr Leu Glu Glu Glu
1               5                   10                  15

Ala Val Arg Leu Phe Ile Glu Trp Leu Lys Asn Gly
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      group A or B peptide

<400> SEQUENCE: 45

Gly Gln Gly Thr Phe Thr Ser Asp Tyr Ser Arg Gln Met Glu Glu Glu
1               5                   10                  15

Ala Val Arg Leu Phe Ile Glu Trp Leu Lys Asn Gly
            20                  25

<210> SEQ ID NO 46
<211> LENGTH: 26
<212> TYPE: PRT
<213> ORGANISM: Artificial Sequence
<220> FEATURE:
<223> OTHER INFORMATION: Description of Artificial Sequence: Synthetic
      group A or B peptide
```

```
<400> SEQUENCE: 46

Gly Glu Gly Thr Phe Thr Ser Asp Leu Ser Arg Gln Met Glu Glu Glu
1               5                   10                  15

Ala Val Arg Leu Phe Ile Glu Trp Ala Ala
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      group A or B peptide

<400> SEQUENCE: 47

Ser Gln Gly Thr Phe Thr Ser Asp Tyr Ser Arg Gln Met Glu Glu Glu
1               5                   10                  15

Ala Val Arg Leu Phe Ile Glu Trp Leu Met Asn Gly
            20                  25

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      group B peptide

<400> SEQUENCE: 48

Gly Glu Gly Thr Phe Thr Ser Asp Leu Ser Arg Gln Met Glu Glu Glu
1               5                   10                  15

Ala Val Arg Leu Phe Ile Glu Trp
            20

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      group B peptide

<400> SEQUENCE: 49

Ser Gln Gly Thr Phe Thr Ser Asp Tyr Ser Arg Tyr Leu Asp
1               5                   10

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cccggccccc gcggccgcta ttcgaaatac                                   30

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 51
gaacggtccg gaggacgtcg actcttaaga tag                    33

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cagcgacacc gaccgtcccc ccgtacttaa ggcc                   34

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctaaccgact ctcggggaag actgagctcg cc                     32

<210> SEQ ID NO 54
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (2)..(2)
<223> OTHER INFORMATION: Aib (aminosiobutyric acid), d-alanine, glycine,
      Sar(N-methylglycine), serine or d-serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid

```
<220> FEATURE:
<221> NAME/KEY: MOD_RES
<222> LOCATION: (16)..(16)
<223> OTHER INFORMATION: Glutamic acid, serine, alpha-methyl-glutamic
      acid or not present
<220> FEATURE:
<221> NAME/KEY: MOD_RES
<222> LOCATION: (17)..(17)
<223> OTHER INFORMATION: Glutamine, glutamic acid, lysine, arginine,
      serine or not present
<220> FEATURE:
<221> NAME/KEY: MOD_RES
<222> LOCATION: (18)..(18)
<223> OTHER INFORMATION: Alanine, arginine, valine or not present
<220> FEATURE:
<221> NAME/KEY: MOD_RES
<222> LOCATION: (19)..(19)
<223> OTHER INFORMATION: Alanine, arginine, serine, valine or not
      present
<220> FEATURE:
<221> NAME/KEY: MOD_RES
<222> LOCATION: (20)..(20)
<223> OTHER INFORMATION: Lysine, glutamine, arginine,
      alpha-methyl-glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
      present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, lysine,
      glutamine, alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, serine, valine or
      not present
<220> FEATURE:
<221> NAME/KEY: MOD_RES
<222> LOCATION: (27)..(27)
<223> OTHER INFORMATION: Alanine, lysine, methionine, glutamine,
      arginine or not present
<220> FEATURE:
<221> NAME/KEY: MISC_FEATURE
<222> LOCATION: (28)..(28)
<223> OTHER INFORMATION: May or may not be present
<220> FEATURE:
<221> NAME/KEY: MOD_RES
<222> LOCATION: (29)..(29)
<223> OTHER INFORMATION: Alanine, glycine, threonine or not present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MOD_RES
<222> LOCATION: (31)..(40)
<223> OTHER INFORMATION: Alanine, glycine, serine or not present
<220> FEATURE:
<221> NAME/KEY: MISC_FEATURE
<222> LOCATION: (31)..(40)
<223> OTHER INFORMATION: This region may encompass 2 to 10 amino acids,
      wherein some positions may be absent
```

-continued

```
<220> FEATURE:
<221> NAME/KEY: MISC_FEATURE
<222> LOCATION: (41)..(60)
<223> OTHER INFORMATION: This region may encompass 8 to 20 amino acids
      including "KRNRNNIA" or "GPSSGAPPPS" or "GPSSGAPPPSK" or
      "HSQGTFTSDYSKYLD" or "HSQGTFTSDYSRYLDK" or "HGEGTFTSDLSKQMEEEAVK,"
<220> FEATURE:
<221> NAME/KEY: MISC_FEATURE
<222> LOCATION: (41)..(60)
<223> OTHER INFORMATION: Continued from above; wherein some or all
      positions may be absent
<220> FEATURE:
<223> OTHER INFORMATION: See specification as filed for detailed
      description of substitutions and preferred embodiments

<400> SEQUENCE: 54

Xaa Xaa Xaa Gly Thr Phe Thr Ser Asp Xaa Xaa Xaa Xaa Xaa Xaa Xaa
1               5                   10                  15

Xaa Xaa Xaa Xaa Xaa Phe Xaa Xaa Trp Xaa Xaa Asn Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa
        50                  55                  60

<210> SEQ ID NO 55
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 26 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or "GQGTFTSDYSRYLEEEAVRLFIEWLKNG" or
      "GQGTFTSDYSRQMEEEAVRLFIEWLKNG"
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG,"
      wherein some positions may be absent
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
<223> OTHER INFORMATION: See specification as filed for detailed
      description of substitutions and preferred embodiments

<400> SEQUENCE: 55

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa
            35                  40
```

```
<210> SEQ ID NO 56
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 14 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or "GQGTFTSDYSRYLEEEAVRLFIEWLKNG" or
      "GQGTFTSDYSRQMEEEAVRLFIEWLKNG"
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG" or
      "GEGTFTSDLSRQMEEEAVRLFIEW" or "SQGTFTSDYSRYLD," wherein some
      positions may be absent
<220> FEATURE:
<221> NAME/KEY: MOD_RES
<222> LOCATION: (30)..(39)
<223> OTHER INFORMATION: Alanine, glycine, serine or not present
<220> FEATURE:
<221> NAME/KEY: MISC_FEATURE
<222> LOCATION: (30)..(39)
<223> OTHER INFORMATION: This region may encompass 2 to 10 amino acids,
      wherein some positions may be absent
<220> FEATURE:
<221> NAME/KEY: MISC_FEATURE
<222> LOCATION: (40)..(59)
<223> OTHER INFORMATION: This region may encompass 15 to 20 amino acids
      including "HSQGTFTSDYSKYLD" or "HSQGTFTSDYSRYLDK" or
      "HGEGTFTSDLSKQMEEEAVK," wherein some positions may be absent
<220> FEATURE:
<223> OTHER INFORMATION: See specification as filed for detailed
      description of substitutions and preferred embodiments

<400> SEQUENCE: 56

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55

<210> SEQ ID NO 57
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (16)..(16)
<223> OTHER INFORMATION: Serine, glutamic acid or arginine
```

```
<220> FEATURE:
<221> NAME/KEY: MOD_RES
<222> LOCATION: (17)..(17)
<223> OTHER INFORMATION: Arginine, glutamic acid or serine
<220> FEATURE:
<221> NAME/KEY: MOD_RES
<222> LOCATION: (18)..(18)
<223> OTHER INFORMATION: Arginine, alanine or valine
<220> FEATURE:
<221> NAME/KEY: MOD_RES
<222> LOCATION: (19)..(19)
<223> OTHER INFORMATION: Arginine, valine or serine
<220> FEATURE:
<221> NAME/KEY: MOD_RES
<222> LOCATION: (20)..(20)
<223> OTHER INFORMATION: Glutamine, arginine or lysine
<220> FEATURE:
<221> NAME/KEY: MOD_RES
<222> LOCATION: (26)..(26)
<223> OTHER INFORMATION: Isoleucine, valine or serine
<220> FEATURE:
<221> NAME/KEY: MOD_RES
<222> LOCATION: (27)..(27)
<223> OTHER INFORMATION: Methionine, arginine or glutamine
<220> FEATURE:
<221> NAME/KEY: MOD_RES
<222> LOCATION: (29)..(29)
<223> OTHER INFORMATION: Threonine, glycine or alanine
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
<223> OTHER INFORMATION: See specification as filed for detailed
      description of substitutions and preferred embodiments

<400> SEQUENCE: 57

Xaa Ser Gln Gly Thr Phe Thr Ser Asp Tyr Ser Lys Tyr Leu Asp Xaa
1               5                   10                  15

Xaa Xaa Xaa Xaa Leu Phe Val Gln Trp Xaa Xaa Asn Xaa Xaa Xaa Xaa
            20                  25                  30

Xaa Xaa Xaa Xaa Xaa Xaa Xaa Xaa
        35                  40

<210> SEQ ID NO 58
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (2)..(2)
<223> OTHER INFORMATION: Serine, Aib, Sar, d-alanine or d-serine
<220> FEATURE:
<221> NAME/KEY: MOD_RES
<222> LOCATION: (16)..(16)
<223> OTHER INFORMATION: Serine or glutamic acid
<220> FEATURE:
<221> NAME/KEY: MOD_RES
<222> LOCATION: (17)..(17)
<223> OTHER INFORMATION: Arginine or lysine
<220> FEATURE:
<221> NAME/KEY: MOD_RES
<222> LOCATION: (20)..(20)
<223> OTHER INFORMATION: Glutamine or lysine
```

```
<220> FEATURE:
<221> NAME/KEY: MOD_RES
<222> LOCATION: (21)..(21)
<223> OTHER INFORMATION: Aspartic acid or glutamic acid
<220> FEATURE:
<221> NAME/KEY: MOD_RES
<222> LOCATION: (24)..(24)
<223> OTHER INFORMATION: Glutamine, cysteine or lysine
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
<222> LOCATION: (31)..(41)
<223> OTHER INFORMATION: This region may encompass 8 to 11 amino acids
      including "KRNRNNIA" or "GPSSGAPPPS" or "GPSSGAPPPSK," wherein
      some or all positions may be absent
<220> FEATURE:
<223> OTHER INFORMATION: See specification as filed for detailed
      description of substitutions and preferred embodiments

<400> SEQUENCE: 58

Xaa Xaa Gln Gly Thr Phe Thr Ser Asp Tyr Ser Lys Tyr Leu Asp Xaa
1               5                   10                  15

Xaa Arg Ala Xaa Xaa Phe Val Xaa Trp Leu Met Asn Thr Xaa Xaa Xaa
            20                  25                  30

Xaa Xaa Xaa Xaa Xaa Xaa Xaa Xaa Xaa
        35                  40

<210> SEQ ID NO 59
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, 4-imidazoacetyl
      or tyrosine
<220> FEATURE:
<221> NAME/KEY: MOD_RES
<222> LOCATION: (2)..(2)
<223> OTHER INFORMATION: Aib(aminosiobutyric acid), glycine, serine or
      d-serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid
```

```
<220> FEATURE:
<221> NAME/KEY: MOD_RES
<222> LOCATION: (16)..(16)
<223> OTHER INFORMATION: Glutamic acid, alpha-methyl-glutamic acid or
      not present
<220> FEATURE:
<221> NAME/KEY: MOD_RES
<222> LOCATION: (17)..(17)
<223> OTHER INFORMATION: Glutamine, glutamic acid, lysine, arginine or
      not present
<220> FEATURE:
<221> NAME/KEY: MOD_RES
<222> LOCATION: (18)..(18)
<223> OTHER INFORMATION: Alanine, arginine or not present
<220> FEATURE:
<221> NAME/KEY: MOD_RES
<222> LOCATION: (19)..(19)
<223> OTHER INFORMATION: Alanine, valine or not present
<220> FEATURE:
<221> NAME/KEY: MOD_RES
<222> LOCATION: (20)..(20)
<223> OTHER INFORMATION: Lysine, glutamine, arginine,
      alpha-methyl-glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
      present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, glutamine,
      alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, valine or not
      present
<220> FEATURE:
<221> NAME/KEY: MOD_RES
<222> LOCATION: (27)..(27)
<223> OTHER INFORMATION: Alanine, lysine, methionine, arginine or not
      present
<220> FEATURE:
<221> NAME/KEY: MISC_FEATURE
<222> LOCATION: (28)..(29)
<223> OTHER INFORMATION: May or may not be present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
<222> LOCATION: (31)..(40)
<223> OTHER INFORMATION: This region may encompass 2 to 10 residues,
      wherein some positions may not be present
<220> FEATURE:
<221> NAME/KEY: MISC_FEATURE
<222> LOCATION: (41)..(60)
<223> OTHER INFORMATION: This region may encompass 8 to 20 amino acids
      including "KRNRNNIA" or "GPSSGAPPPS" or "GPSSGAPPPSK" or
      "HSQGTFTSDYSKYLD" or "HSQGTFTSDYSRYLDK" or "HGEGTFTSDLSKQMEEEAVK,"
      wherein some or
```

```
<220> FEATURE:
<221> NAME/KEY: MISC_FEATURE
<222> LOCATION: (41)..(60)
<223> OTHER INFORMATION: Continued from above; all positions may be
      absent
<220> FEATURE:
<223> OTHER INFORMATION: See specification as filed for detailed
      description of substitutions and preferred embodiments

<400> SEQUENCE: 59

Xaa Xaa Xaa Gly Thr Phe Thr Ser Asp Xaa Xaa Xaa Xaa Xaa Xaa
1               5                   10                  15

Xaa Xaa Xaa Xaa Xaa Phe Xaa Xaa Trp Xaa Xaa Asn Thr Xaa Gly Gly
            20                  25                  30

Gly Gly Gly Gly Gly Gly Gly Gly Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60
```